(12) United States Patent
Naruse

(10) Patent No.: US 8,161,815 B2
(45) Date of Patent: Apr. 24, 2012

(54) ULTRASOUND DIAGNOSTIC APPARATUS

(75) Inventor: Naoyuki Naruse, Mitaka (JP)

(73) Assignee: Hitachi Aloka Medical, Ltd., Mitaka-shi, Tokyo (JP)

( * ) Notice: Subject to any disclaimer, the term of this patent is extended or adjusted under 35 U.S.C. 154(b) by 755 days.

(21) Appl. No.: 12/062,815

(22) Filed: Apr. 4, 2008

(65) Prior Publication Data

US 2008/0249406 A1    Oct. 9, 2008

(30) Foreign Application Priority Data

| Apr. 6, 2007 | (JP) | 2007-100254 |
| Apr. 6, 2007 | (JP) | 2007-100270 |
| Apr. 6, 2007 | (JP) | 2007-100285 |
| Apr. 6, 2007 | (JP) | 2007-100300 |
| Apr. 6, 2007 | (JP) | 2007-100413 |
| Apr. 6, 2007 | (JP) | 2007-100420 |

(51) Int. Cl.
 *G01D 11/24* (2006.01)
 *G01L 19/14* (2006.01)
 *G01P 1/02* (2006.01)

(52) U.S. Cl. .......................................................... 73/431

(58) Field of Classification Search ...................... 73/431
 See application file for complete search history.

(56) References Cited

U.S. PATENT DOCUMENTS

| 4,809,393 A * | 3/1989 | Goodrich et al. ............... 15/323 |
| 4,842,531 A | 6/1989 | Takemura |
| 4,901,261 A | 2/1990 | Fuhs |
| 5,268,817 A | 12/1993 | Miyagawa et al. |
| 5,383,138 A | 1/1995 | Motoyama et al. |
| 5,566,048 A * | 10/1996 | Esterberg et al. ........ 361/679.27 |
| 5,646,818 A * | 7/1997 | Hahn ...................... 361/679.09 |
| 6,154,359 A | 11/2000 | Kamikakai et al. |
| 6,436,040 B1 * | 8/2002 | Collamore et al. ........... 600/437 |
| 6,440,076 B1 | 8/2002 | Sudol et al. |
| 6,540,685 B1 | 4/2003 | Rhoads et al. |
| 6,561,979 B1 | 5/2003 | Wood et al. |
| 6,665,176 B2 | 12/2003 | Amemiya et al. |
| 6,821,250 B2 | 11/2004 | Mesaros et al. |

(Continued)

FOREIGN PATENT DOCUMENTS

CN    1397858 A    2/2003

(Continued)

OTHER PUBLICATIONS

European Search Report dated Aug. 29, 2008, issued in corresponding European Patent Application No. 08005852.2.

(Continued)

*Primary Examiner* — Lisa Caputo
*Assistant Examiner* — Jamel Williams
(74) *Attorney, Agent, or Firm* — Westerman, Hattori, Daniels & Adrian, LLP

(57) ABSTRACT

In a transportable ultrasound diagnostic apparatus, a body to which a display unit on which an ultrasound image is displayed is integrated and an operation panel are connected by a connecting member. The body and the operation panel are supported by a body supporting stub and an operation panel supporting stub, which are separate supporting stubs, on the connecting member in a pivotable manner around center axes of the supporting stubs. The ultrasound diagnostic apparatus is used in an open state in which the operation panel is pulled down to the front side. The operation panel is pivoted to close with the body, resulting in a storage state.

25 Claims, 17 Drawing Sheets

U.S. PATENT DOCUMENTS

| | | | |
|---|---|---|---|
| 6,888,534 B1 * | 5/2005 | Northway | 345/169 |
| 7,141,020 B2 | 11/2006 | Poland et al. | |
| 7,584,830 B2 * | 9/2009 | Smith | 190/11 |
| 7,724,543 B2 | 5/2010 | Ozawa et al. | |
| 2002/0181193 A1 | 12/2002 | Amemiya et al. | |
| 2003/0140457 A1 | 7/2003 | Kida | |
| 2003/0236463 A1 | 12/2003 | Mesaros et al. | |
| 2004/0041499 A1 | 3/2004 | Donovan et al. | |
| 2004/0150963 A1 | 8/2004 | Holmberg et al. | |

FOREIGN PATENT DOCUMENTS

| | | |
|---|---|---|
| EP | 0463585 A2 | 1/1992 |
| GB | 2392709 A | 3/2004 |
| JP | 59-116009 U | 8/1984 |
| JP | 1-84615 U | 6/1989 |
| JP | 2-038710 A | 2/1990 |
| JP | 2-101274 A | 4/1990 |
| JP | 2-101583 U | 8/1990 |
| JP | 3-288917 A | 12/1991 |
| JP | 4-50012 U | 4/1992 |
| JP | 5-57431 U | 7/1993 |
| JP | 6-274244 A | 9/1994 |
| JP | 8-106342 A | 4/1996 |
| JP | 9-021275 A | 1/1997 |
| JP | 9-034588 A | 2/1997 |
| JP | 10-005221 A | 1/1998 |
| JP | 2000-041951 A | 2/2000 |
| JP | 2001-065543 A | 3/2001 |
| JP | 2002-215267 A | 7/2002 |
| JP | 2002-272739 A | 9/2002 |
| JP | 2002-368443 A | 12/2002 |
| JP | 2003-513546 A | 4/2003 |
| JP | 2004-003594 A | 1/2004 |
| JP | 2004-053588 A | 2/2004 |
| JP | 2005-517515 A | 6/2005 |
| WO | 01/33816 A1 | 5/2001 |
| WO | 2006-129350 A1 | 12/2006 |

OTHER PUBLICATIONS

European Search Report dated Sep. 26, 2011, issued in corresponding European Patent Application No. 11005218.0.

Notice of Allowance dated Jan. 24, 2012, issued in corresponding Japanese Patent Application No. 2007-100270. w/Partial English Translation.

Notice of Allowance dated Jan. 24, 2012, issued in corresponding Japanese Patent Application No. 2007-100300. w/Partial English Translation.

Japanese Office Action dated Jan. 17, 2012, issued in corresponding Japanese Patent Application No. 2007-100254.

Japanese Office Action dated Jan. 17, 2012, issued in corresponding Japanese Patent Application No. 2007-100285.

Japanese Office Action dated Jan. 17, 2012, issued in corresponding Japanese Patent Application No. 2007-100413.

Japanese Office Action dated Jan. 17, 2012, issued in corresponding Japanese Patent Application No. 2007-100420.

* cited by examiner

ULTRASOUND DIAGNOSTIC APPARATUS

BACKGROUND OF THE INVENTION

1. Field of the Invention

The present invention relates to an ultrasound diagnostic apparatus, and in particular, to a transportable ultrasound diagnostic apparatus which can be carried.

2. Description of the Related Art

A transportable ultrasound diagnostic apparatus which can be easily carried and which can be used in a location to which the ultrasound diagnostic apparatus is carried is known. For example, JP Hei 10-5221 A discloses a transportable ultrasound diagnostic apparatus having a keyboard unit which is pivotably supported on a body having an integrated display unit and which is opened and closed through pivoting of the keyboard unit. More specifically, the keyboard unit is pivotably supported near a lower end of a front side of the body, and the keyboard unit positioned extending from the front side of the body toward the front side can be pivoted to the upper direction, to close the keyboard unit in a manner to oppose the front side on which the display unit is provided, resulting in a storage state. The apparatus is carried in this state by holding a handle placed on an upper surface of the body.

In the device described in JP Hei 10-5221 A, the display unit is fixed, and the orientation of the display unit cannot be changed as desired by the operator, and thus the operability is inferior.

SUMMARY OF THE INVENTION

The present invention advantageously provides an ultrasound diagnostic apparatus having a superior operability and a superior transportability. According to another aspect of the present invention, an ultrasound diagnostic apparatus having a superior storage characteristic is provided.

According to one aspect of the present invention, there is provided a transportable ultrasound diagnostic apparatus comprising a body to which a display unit is integrated, an operation panel provided for operation of the ultrasound diagnostic apparatus, and a connecting member to which the body and the operation panel are pivotably linked around axes which differ from each other, and which connects the body and the operation panel.

According to another aspect of the present invention, there is provided a transportable ultrasound diagnostic apparatus comprising a body, an operation panel provided for operation of the ultrasound diagnostic apparatus, and a connecting member to which the body and the operation panel are pivotably linked around axes which differ from each other, and which connects the body and the operation panel, wherein the body and the operation panel can be pivoted to an upright state and can be closed, to result in a storage state. According to another aspect of the present invention, it is preferable that the ultrasound diagnostic apparatus further comprises a handle which is placed on an upper portion of the body and which is raised and used during carriage, a slide rod which engages the handle and slides along the body, and which has a follower, and a guide plate which is fixed to the connecting member and which has a guide channel which receives the follower, wherein, when the follower is positioned within the guide channel, the follower moves in the guide channel with raising of the handle and is guided by the guide channel so that the body is pivoted to the upright state.

According to another aspect of the present invention, there is provided a ultrasound diagnostic apparatus comprising an operation panel which pivots around a horizontal axis with respect to a supporting member so that the operation panel can be opened and closed, a frictional torque applying unit which applies a frictional torque which resists an opening operation of the operation panel and which blocks pivoting of the operation panel due to a weight of the operation panel until the operation panel is opened to a first angle, and an elastic torque applying unit which applies a torque by an elastic force in a closing direction of the operation panel when the operation panel is opened to an angle of greater than or equal to a second angle.

According to another aspect of the present invention, there is provided a ultrasound diagnostic apparatus comprising an operation panel which pivots around a horizontal axis with respect to a supporting member so that the operation panel can be opened and closed, a hinge shaft which is fixed on the supporting member and which is placed coaxially with the pivoting axis of the operation panel, a frictional bush which is fixed on the operation panel, through which the hinge shaft is inserted, and which generates a frictional torque through relative rotation with the hinge shaft, and a torsion spring which has a helical portion through which the hinge axis passes, a first end which extends from the helical portion in parallel to the hinge shaft, and a second end which extends from the helical portion in a direction diverting from the hinge shaft. The hinge shaft has a large-diameter portion which is thicker than a portion through which the torsion spring passes and which has a recess which receives the first end of the torsion spring, the first end can be moved in the recess in the circumferential direction within a range defined by two end surfaces of the recess in the circumferential direction, and the operation panel comprises an engagement plate which engages the second end of the torsion spring. The frictional torque generated by the frictional bush blocks pivoting of the operation panel due to a weight of the operation panel until the operation panel is opened to a predetermined angle, the first end of the torsion spring contacts one end surface of the recess receiving the first end when the operation panel is opened to the predetermined angle, and a torque is applied by the torsion spring in a direction to close the operation panel when the operation panel is opened to an angle of greater than or equal to the predetermined angle.

According to another aspect of the present invention, there is provided a transportable ultrasound diagnostic apparatus comprising a body, an operation panel provided for operation of the ultrasound diagnostic apparatus, a connecting member to which the body and the operation panel are pivotably linked around axes which differ from each other, and which connects the body and the operation panel. The body and the operation panel can be pivoted to an upright state and can be closed, to result in a storage state. When the operation panel is closed, the operation panel pushes the body to pivot the body toward the upright state.

According to another aspect of the present invention, there is provided a holder for a ultrasound diagnostic apparatus, the holder being attached to a transportable ultrasound diagnostic apparatus comprising a body to which a display unit is integrated, an operation panel provided for an operation of the ultrasound diagnostic apparatus, and a connecting member which connects the body and the operation panel. The holder stores an ultrasonic probe of the ultrasound diagnostic apparatus.

According to another aspect of the present invention, there is provided a transportable ultrasound diagnostic apparatus comprising a body to which a display unit is integrated, an operation panel provided for an operation of the ultrasound diagnostic apparatus, and a connecting member which connects the body and the operation panel, wherein a holder which stores a ultrasonic probe can be attached to the connecting member.

According to another aspect of the present invention, there is provided a transportable ultrasound diagnostic apparatus comprising a body to which a display unit is integrated, an operation panel provided for an operation of the ultrasound diagnostic apparatus, and a connecting member which connects the body and the operation panel. The body and the operation panel can be closed with a display screen of the display unit and an operation surface of the operation panel at the inside. A probe cable of an ultrasonic probe which is used in the ultrasound diagnostic apparatus is wound around and fixed to the body and the operation panel in a manner to bundle the closed body and operation panel.

BRIEF DESCRIPTION OF THE DRAWINGS

Exemplary embodiment(s) of the present invention will be described in detail based on the following figures, wherein.

DESCRIPTION OF PREFERRED EMBODIMENT

Figure 1:
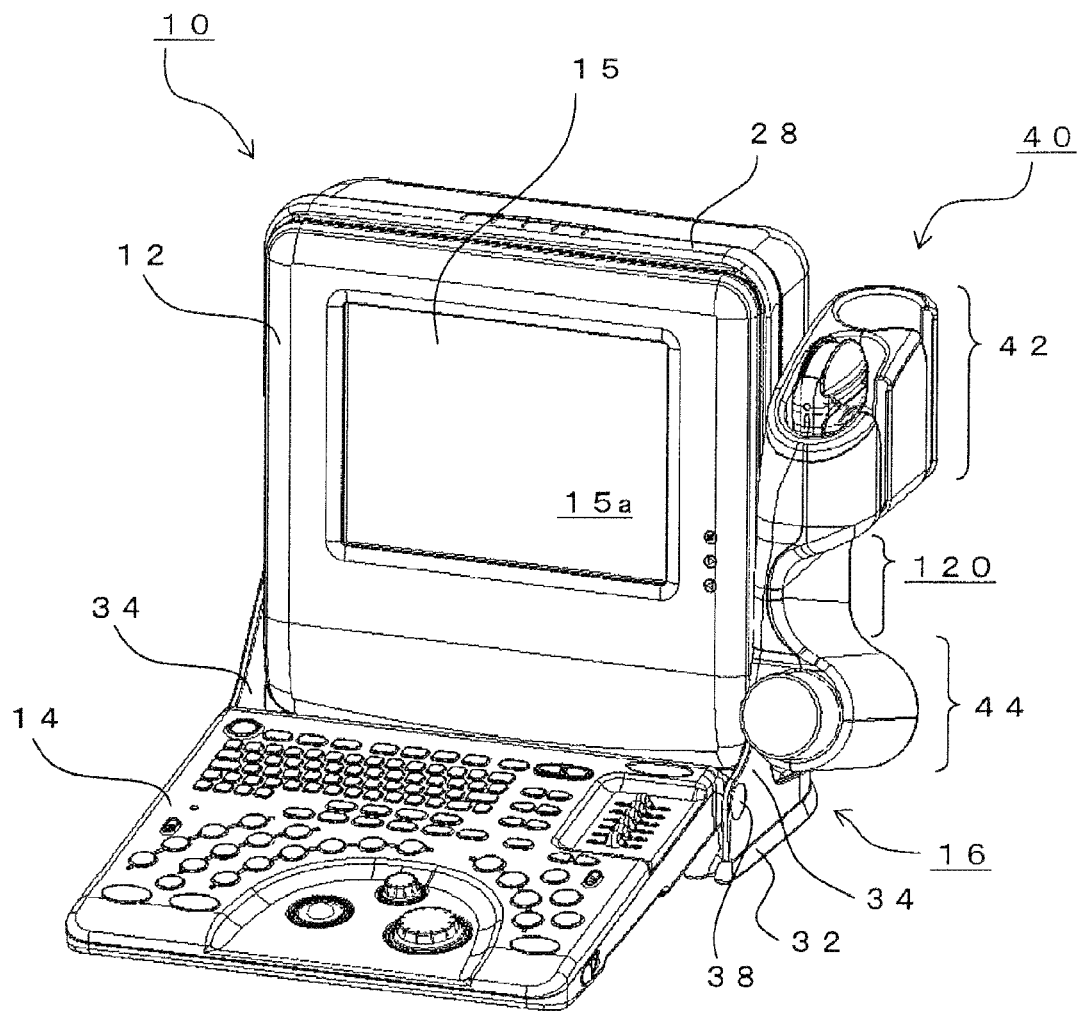
FIG. 1 is a front side perspective view of an open state of an ultrasound diagnostic apparatus according to a preferred embodiment of the present invention.
Figure 2:
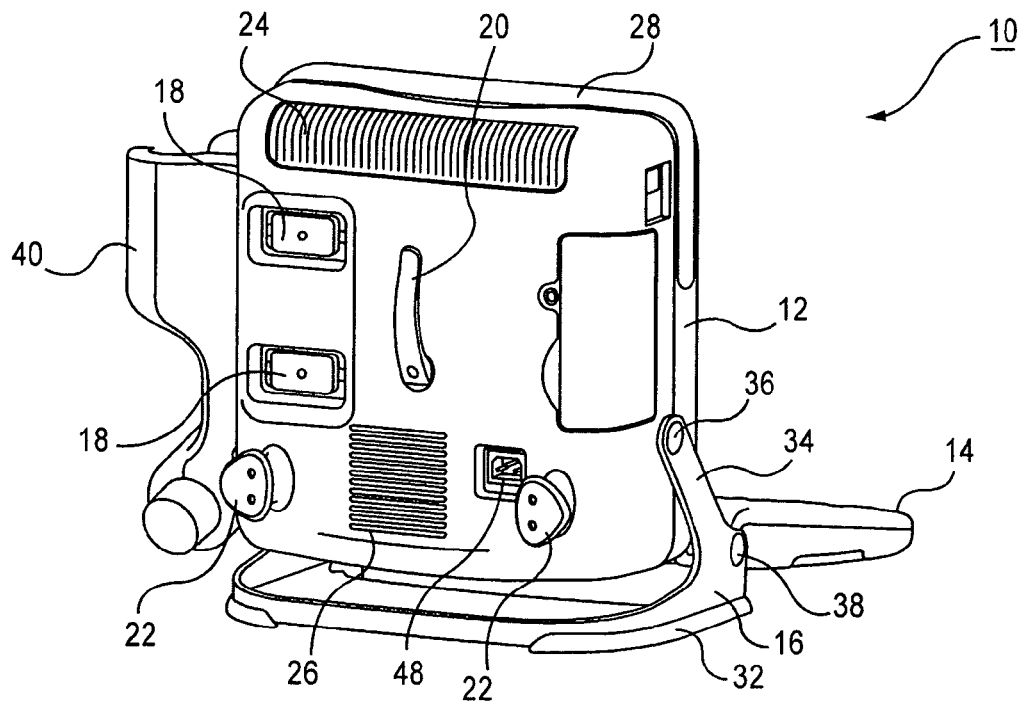
FIG. 2 is a rear side perspective view of an open state of an ultrasound diagnostic apparatus according to a preferred embodiment of the present invention.
Figure 3:
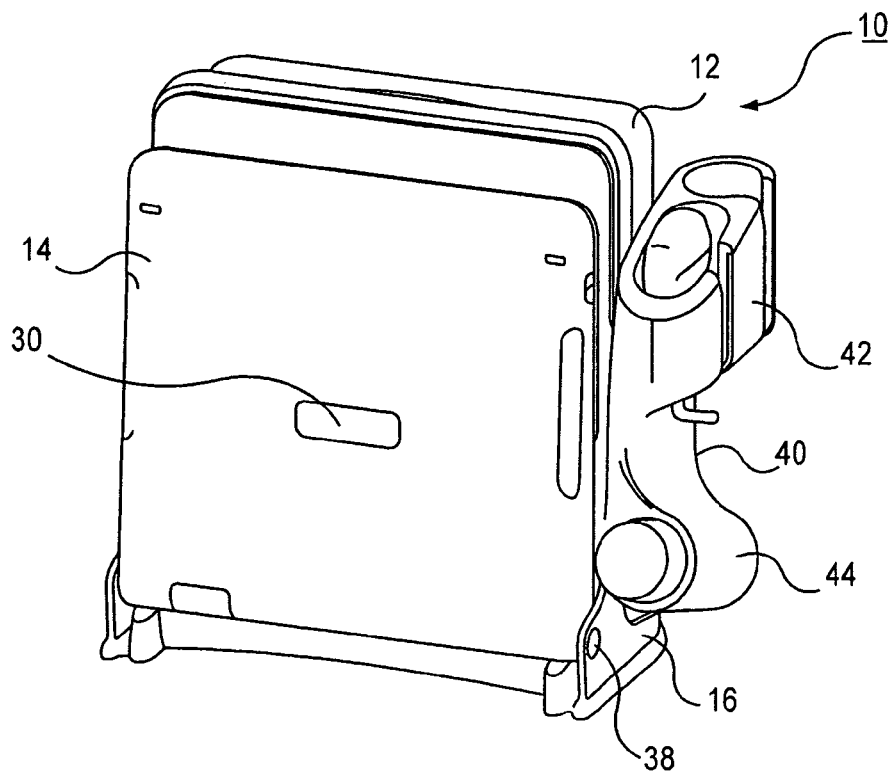
FIG. 3 is a front side perspective view of a storage state of an ultrasound diagnostic apparatus according to a preferred embodiment of the present invention.
Figure 4:
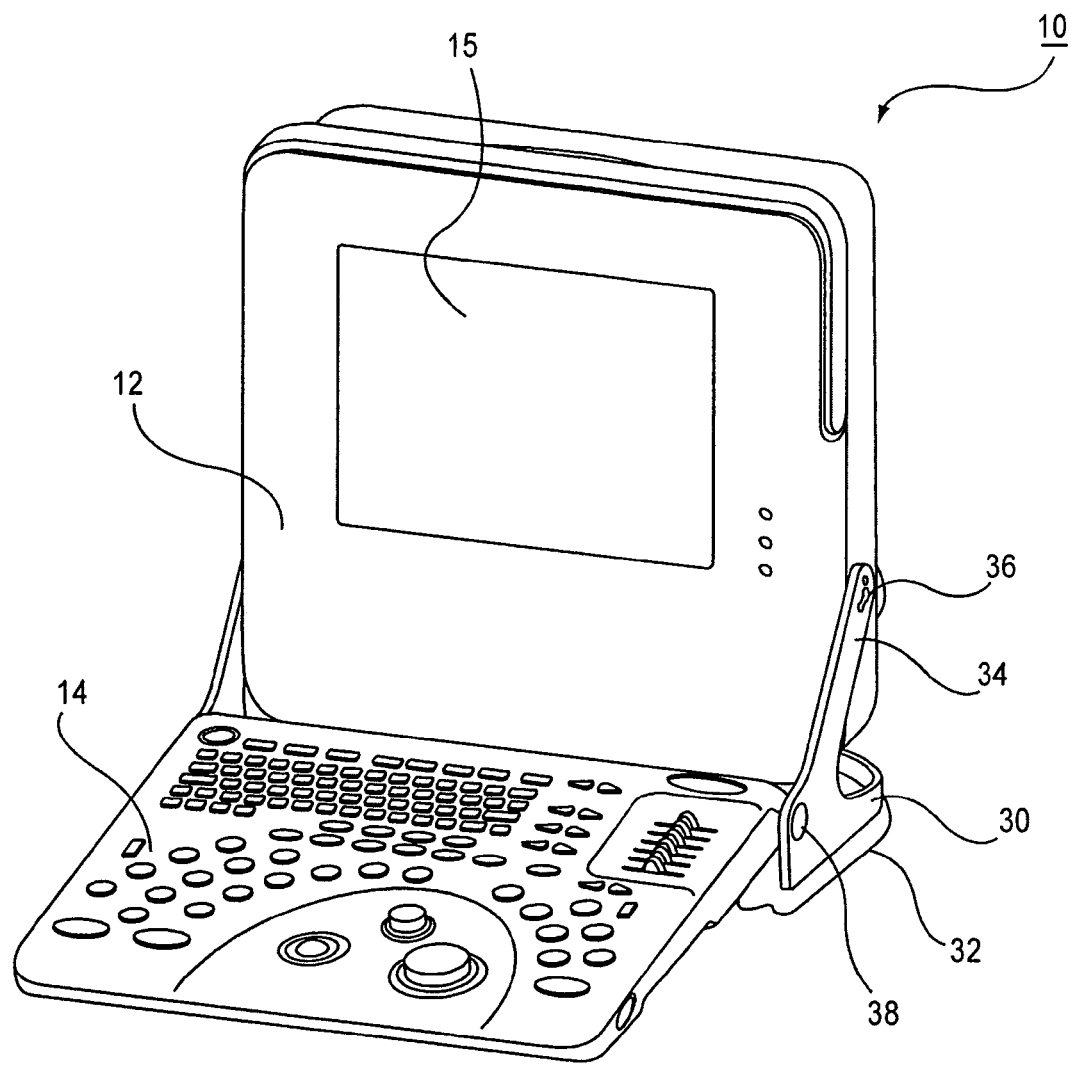
FIG. 4 is a front side perspective view of an ultrasound diagnostic apparatus according to a preferred embodiment of the present invention in a state in which a probe holder is removed.

A preferred embodiment of the present invention will now be described with reference to the drawings. FIGS. 1-4 are perspective views showing an external appearance of a ultrasound diagnostic apparatus 10 according to a preferred embodiment of the present invention. FIG. 1 is a front side perspective view, FIG. 2 is a rear side perspective view, FIG. 3 is a front side perspective view showing a state in which an operation panel is stored, and FIG. 4 is a front side perspective view showing a state in which a probe holder is removed.

The ultrasound diagnostic apparatus 10 comprises a body 12 storing electronic circuit components such as an image processing circuit and a power supply circuit, an operation panel 14 for an operation of the apparatus, and a connecting frame 16 which supports the body 12 and the operation panel 14 pivotably around axes which differ from each other and which connects the body 12 and the operation panel 14. The body 12 has an approximate box shape in which corners of a rectangular parallelepiped are smoothed. A flat-panel display unit 15 such as a liquid crystal display device is integrated to the body 12 and a display screen 15a of the display device 15 is placed on one surface of the box shape. The surface on which the display screen is provided is referred to as a front surface and a surface opposite to the front surface is referred to as a back surface. On the back surface, two receptacles 18 to which a connector of an ultrasonic probe is linked are placed and a hook 20 on which a cable of the ultrasonic probe is hooked and which fixes the cable is provided. In addition, a pair of cable winding projections 22 around which a power supply cable is wound and which stores the power supply cable when the apparatus is not in use are provided at a portion near a lower side of the back surface side. Near an upper side of the back surface, an outside air introduction port 24 is provided and a discharge port 26 is provided at a center portion near the lower side. A fan is placed inside of the discharge port 26. When the fan is operated, air which is sucked from the outside air introduction port 24 passes through the inside of the body, and is discharged from the discharge port 26. A handle 28 which is used when the apparatus is carried is placed on an upper surface side of the body 12. The handle 28 can be raised from the illustrated state, and is used in the raised state during carriage.

On a front side of the operation panel 14, operation elements such as a keyboard for inputting a character such as a letter or a number, a slide switch for selecting and adjusting various functions for ultrasound diagnosis, a push-button type switch, a dial and a track ball are provided. The ultrasound diagnostic apparatus 10 is operated by operating the operation elements. On the back surface of the operation panel 14 shown in FIG. 3, that is, on the surface which faces the outside when the body 12 and the operation panel 14 are closed, a light emitting unit 30 is placed. The light emitting unit 30 comprises a front surface panel flush-mounted with the operation panel 14 and made of a transparent, semitransparent, or translucent material and a light source such as an LED which is placed at the back of the front surface panel. A light-shielding portion may be provided on the front surface panel, so that light from the light source is suitably shielded and a predetermined character, diagram, etc. maybe formed. The light source emits light when the power supply of the ultrasound diagnostic apparatus 10 is in the ON state and is extinguished when the power supply of the ultrasound diagnostic apparatus 10 is in the OFF state. In this manner, the light emitting unit 30 functions as an indicator indicating the ON/OFF states of the power supply. With such a configuration, it is possible to know that the power supply is ON even in the state in which the operation panel 14 is closed, as shown in FIG. 3, and to ensure that the power supply is switched OFF.

The connecting frame 16 comprises a base portion 32 which allows placement of the apparatus on a flat surface such as a top plate of a table, and an arm portion 34 extends from the base portion 32 in an upward direction. Near a tip of the arm portion 34, a body supporting stub 36 which pivotably supports the body 12 is provided. The body 12 can pivot within a predetermined angle range around a center axis of the support stub 36. By making the body 12 pivotable, the body 12 can pivot in both a backward tilt and a forward tilt. It is also desirable to set the pivoting range so that the angle of the backward tilt, that is, a tilt at which the display screen 15a faces upward, can be larger than the angle of the forward tilt. In the ultrasound diagnostic apparatus 10, the body 12 can be tilted from a position in which the display screen 15a is vertical to 10° forward and 30° backward. Because the body 12 can be tilted forward, reflection of illumination or the like on the display screen 15a can be inhibited. In addition, because the ultrasound diagnostic apparatus is used in a form in which the operator views the display screen 15a while contacting an ultrasonic probe on a subject, the viewpoint of the operator may become a low position. In this case also, the configuration to allow forward tilt of the display screen is advantageous.

The body supporting stub 36 supports the body at a position distanced in an upward direction from a position near a lower end of the body 12, and can narrow the movement range of the body 12 by the pivoting. If, however, the body is supported at a position which is too high, even when the body 12 is to be pivoted by moving the body while holding a position near an upper end of the body, the body 12 cannot be pivoted. Therefore, the height at which the body 12 is to be supported is desirably a height greater than or equal to ¼ of the height of the body 12 and less than or equal to ½ of the height of the body 12.

Near a root of the arm portion of the connecting frame 16, an operation panel supporting stub 38 which pivotably supports the operation panel 14 is provided. The operation panel 14 pivots around a center axis of the operation panel supporting stub 38. The operation panel supporting stub 38 supports a rear side of the panel when the operation panel 14 is opened. In this process, the front side of the operation panel 14 can be supported by a surface such as a table and a stage on which the connecting frame 16 is placed. The operation panel 14 can pivot between a state as shown in FIG. 1 or 4 in which the operation panel 14 is tilted toward the front side and the front surface on which various operation elements are provided facing upward and a state as shown in FIG. 3 which is approximately upright. The state shown in FIG. 1 or 4 in which the operation panel 14 is tilted toward the front side is referred to as an "open state" of the ultrasound diagnostic apparatus 10 and a state as shown in FIG. 3 in which the operation panel 14 is set to an upright position and is closed along the body 12 is referred as a "storage state".

In the storage state, the body 12 and the operation panel 14 are in an approximate upright state wherein the surface of the body 12 on which the display screen 15a and a surface of the operation panel 14 on which various operation elements are provided face each other. The ultrasound diagnostic apparatus 10 can be placed on a flat surface such as a table in this orientation. A projection area to a horizontal surface in the storage state is small, and thus the ultrasound diagnostic apparatus 10 can be stored in a narrow storage space.

As described, in the ultrasound diagnostic apparatus 10, the orientation of the display surface of the display unit which is integral with the body can be changed by pivoting the body. In addition, because the connecting member can be placed on a flat surface and the body and the operation panel can be pivoted in this state, it is possible to set the apparatus in a storage state wherein the body and the operation panel are upright. In this storage state, the occupying area becomes small, and thus the apparatus can be stored in a narrow location.

It is also possible to employ a configuration in which the connecting frame 16 is used only for mechanically connecting the body 12 and the operation panel 14. In other words, it is possible to not build in a cable or the like through which an electrical signal, more specifically a signal exchanged between the operation panel 14 and the body 12 and related to operations, is transmitted. This signal is transmitted through an independent cable connecting the body 12 and the operation panel 14, and the function of the ultrasound diagnostic apparatus may be realized by the body 12 and the operation panel 14 without the connecting frame 16.

A holder 40 which stores a probe or the like may be equipped on the connecting frame 16. The holder 40 shown in the drawings comprises a probe receptacle 42 corresponding to two types of ultrasonic probes, and a jelly container receptacle 44 which receives a container of jelly to be applied on a surface of a subject in order to match impedance. Because the holder 40 is equipped on the connecting frame 16, the holder 40 does not move, even when the body 12 and the operation panel 14 are pivoted, and can stably hold the ultrasonic probe and the jelly container. In addition, it is also possible to employ a configuration in which a probe holder is equipped at a left side on the drawing of the body 12. In addition, it is also possible to employ a configuration in which a holder having only a receptacle for the ultrasonic probe is equipped on the right side and a holder which holds the jelly container is equipped on the left side.

Figure 5:
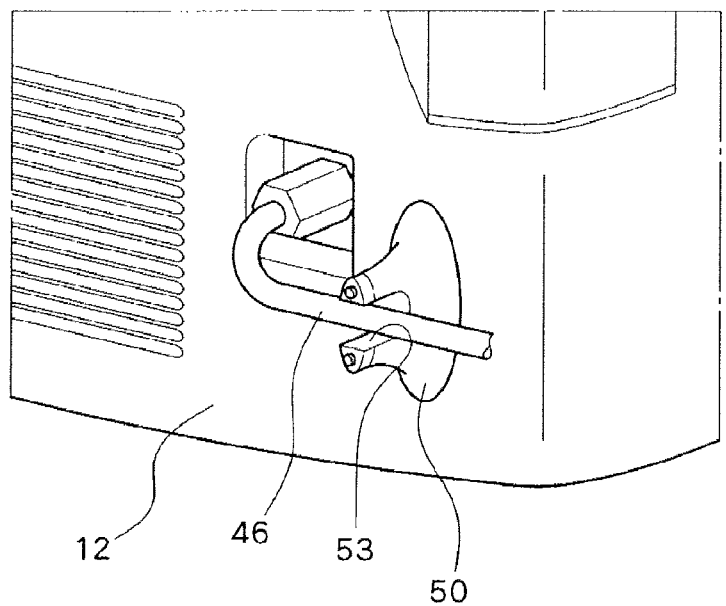
FIG. 5 is an explanatory diagram related to storage of a power supply cable.
Figure 6:
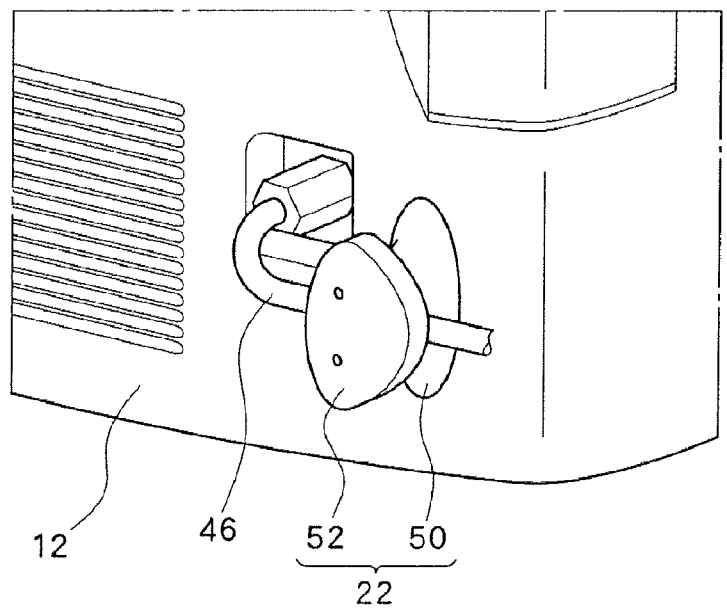
FIG. 6 is an explanatory diagram related to storage of a power supply cable.
Figure 7:
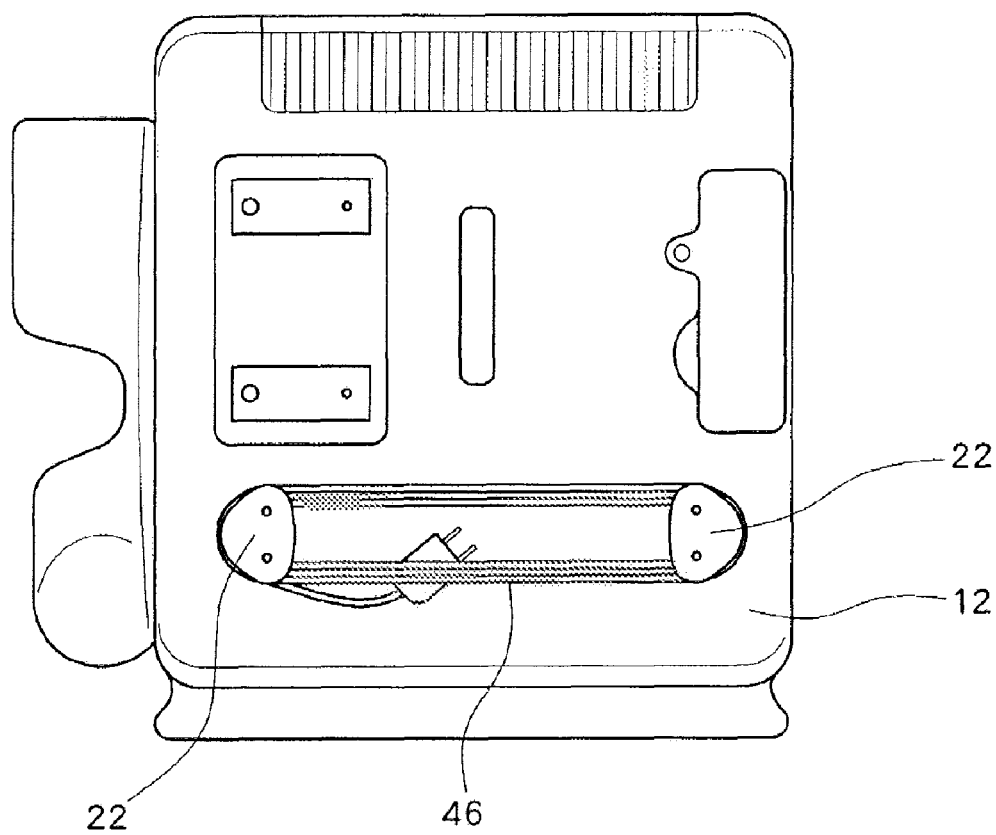
FIG. 7 is an explanatory diagram related to storage of a power supply cable.

FIGS. 5-7 are explanatory diagrams related to storage of a power supply cable 46. On a back surface of the body 12, a power supply cable receptacle 48 (FIG. 2) on which a pin to be electrically connected to the power supply cable is placed is provided. In addition, on the back surface, a pair of cable winding projections 22 for storing the power supply cable 46 by winding the power supply cable 46 is provided. The cable winding projection 22 comprises a pillar-shaped portion 50 projecting from the back surface of the body 12 and a flange portion 52 which is fixed to the tip of the pillar-shaped portion. The flange portion 52 extends to the outside from the tip of the pillar-shaped portion 50 so that a step formed by this structure holds the wound power supply cable. On the pillar-shaped portion 50 on a side near the power supply cable receptacle 48, a channel 53 for pinching the cable is provided from the tip as shown in FIG. 5. After the power supply cable 46 is pinched in the channel as shown in FIG. 5, the flange portion 52 is linked to the pillar-shaped portion 50 as shown in FIG. 6. In this manner, it is possible to prevent the power supply cable 46 from coming loose from the receptacle 48 even when the power supply cable is inadvertently pulled. On the cable winding projection 22 on the opposite side, no channel needs to be provided. As shown in FIG. 7, the power supply cable 46 is wound between two cable winding projections 22, and is stored.

In the ultrasound diagnostic apparatus 10, both the body 12 and the operation panel 14 can pivot, and the ultrasound diagnostic apparatus 10 is advantageous in achieving a compact external shape during carriage. It would be convenient if the body 12 can be set, with a simple operation, to a position suitable for carrying. In addition, when both the body 12 and the operation panel 14 are pivotable, the stability during carriage tends to be reduced. In consideration of these points, the ultrasound diagnostic apparatus 10 of the present embodiment has a mechanism which raises the handle 28 to pivot the body to the upright state and fix the body in the upright position.

Figure 8:
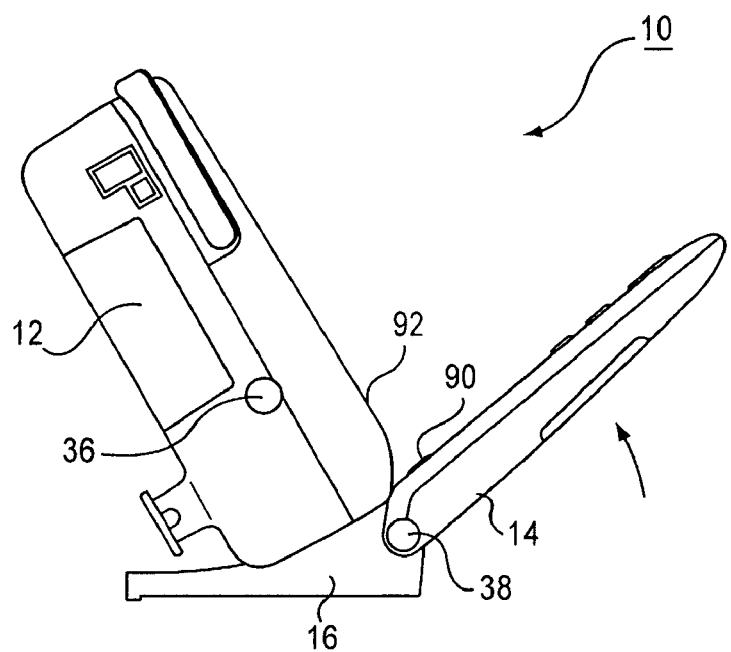
FIG. 8 is a diagram showing a relationship between an operation panel and a body when the apparatus is changed from an open state to a storage state, and particularly showing a state in which the body is backwardly tilted to a maximum angle.
Figure 9:
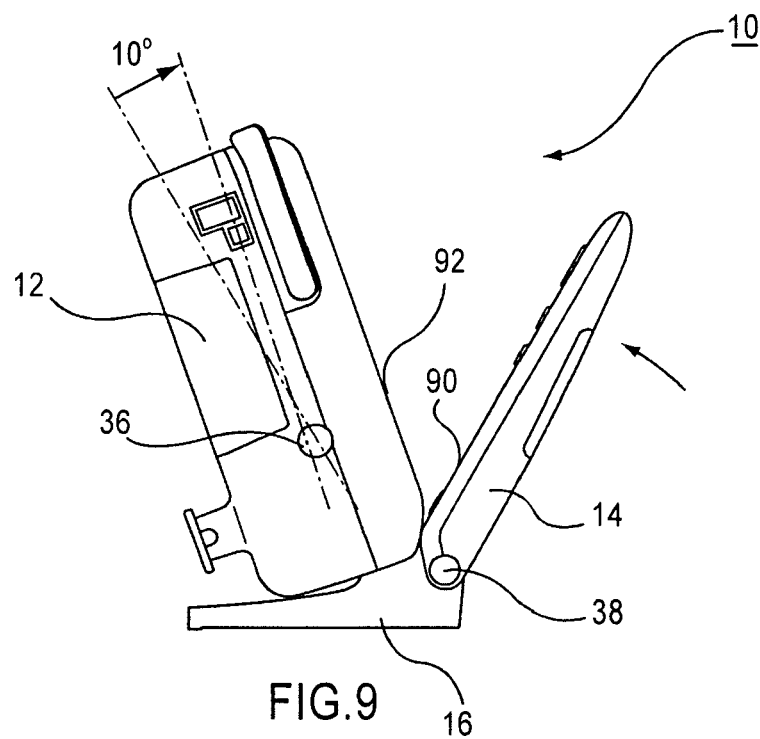
FIG. 9 is a diagram showing a relationship between an operation panel and a body when the apparatus is changed from an open state to a storage state, and showing a state of the body in the middle of standing.

FIGS. 8 and 9 are diagrams showing a state in the middle of transition from the open state to the storage state of the ultrasound diagnostic apparatus 10. In FIGS. 8 and 9, the connecting frame 16 is shown with a part of the connecting frame such as the arm portion 34 omitted, in order to allow a better view of the body 12 and the operation panel 14.

Figure 10:
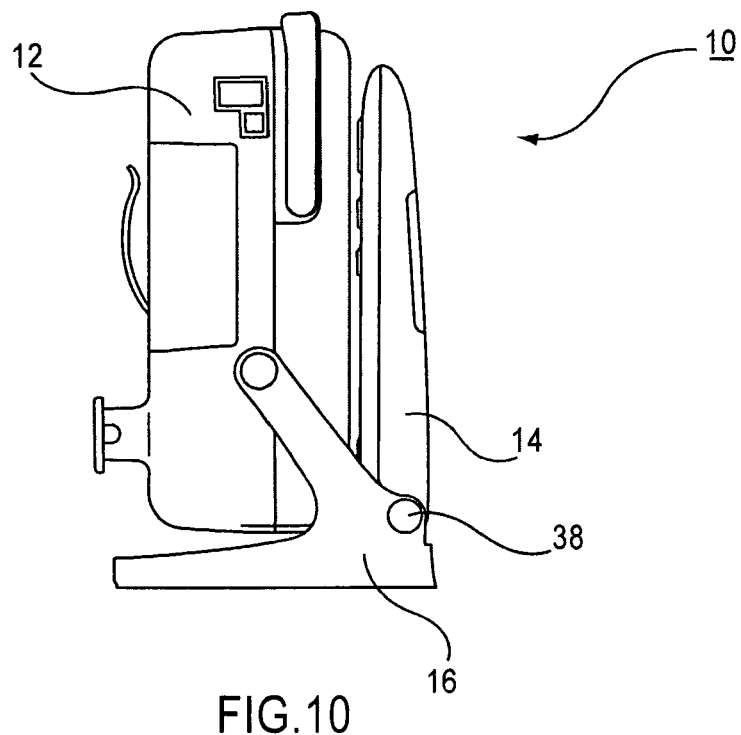
FIG. 10 is a diagram showing a storage state.

As described above, the body 12 of the ultrasound diagnostic apparatus 10 is pivotable on the connecting frame 16 in a predetermined angle range centered at the body supporting stub 36. FIG. 8 shows a state in which the body 12 is backwardly tilted to a maximum angle (with a backward tilt angle of 30°). In this configuration, the display screen 15a is backwardly tilted by 30° with respect to the vertical direction. When the operation panel 14 is raised from an open position such as the position shown in FIG. 1, a front panel member 90 on a front surface (a surface on which an operation switch or the like is placed) of the operation panel 14 contacts a case member 92 near a lower side of the approximate box-shaped body on a front side, at a position shown in FIG. 8. When the operation panel 14 is further raised and pivoted, the operation panel 14 pushes the body 12, to pivot the body 12 in a direction of reducing backward tilt angle of the body. FIG. 9 shows a state with a backward tilt angle of 20°. When the operation panel 14 is further pivoted to the upright state as shown in FIG. 10, the body 12 is also pivoted to an approximately upright state.

Figure 11:
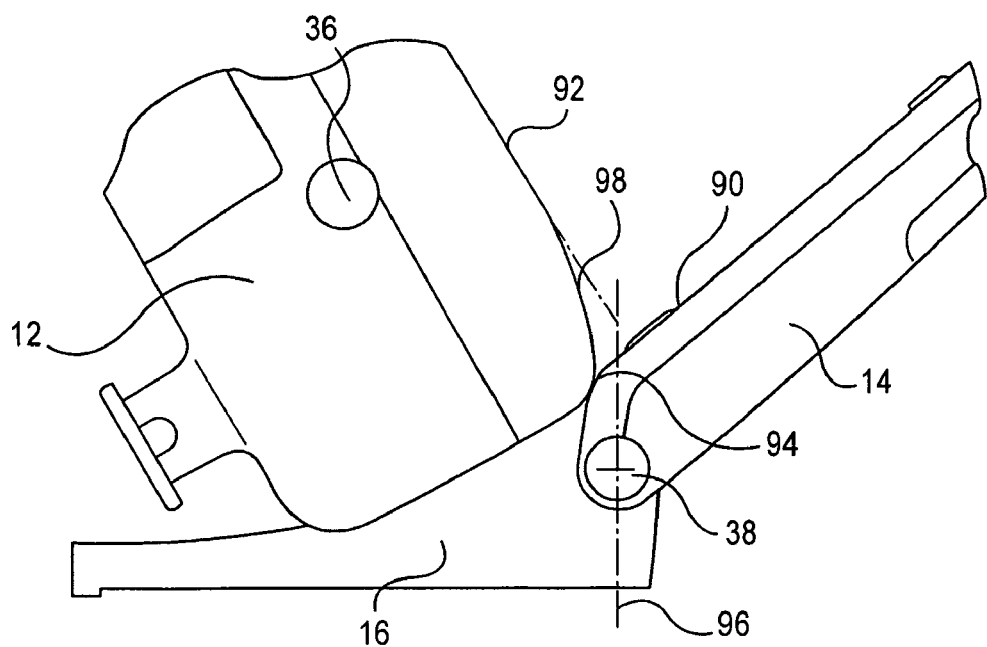
FIG. 11 is a diagram showing a detail around a contact point between an operation panel and a body in the state shown in FIG. 8.

FIG. 11 is a diagram enlarging a portion of FIG. 8 near a contact point between the body 12 and the operation panel 14. A force applied on the body 12 by the operation panel at a contact point 94 between the front panel member 90 of the operation panel and the case member 92 of the body generates a clockwise moment around a center axis of the body supporting stub 36. In other words, the shapes of the front panel member 90 and the case member 92 are determined such that the front panel member 90 and the case member 92 contact each other at a position which generates such a moment. Desirably, the shapes of the members can be determined such that the contact point 94 is at a left side in FIG. 11 from a vertical surface 96 through the axis of the operation panel supporting stub 38. For this purpose, in the ultrasound diagnostic apparatus 10, a sloped surface 98 is formed around a lower side of the case member 92, to round the corner.

Figure 12:
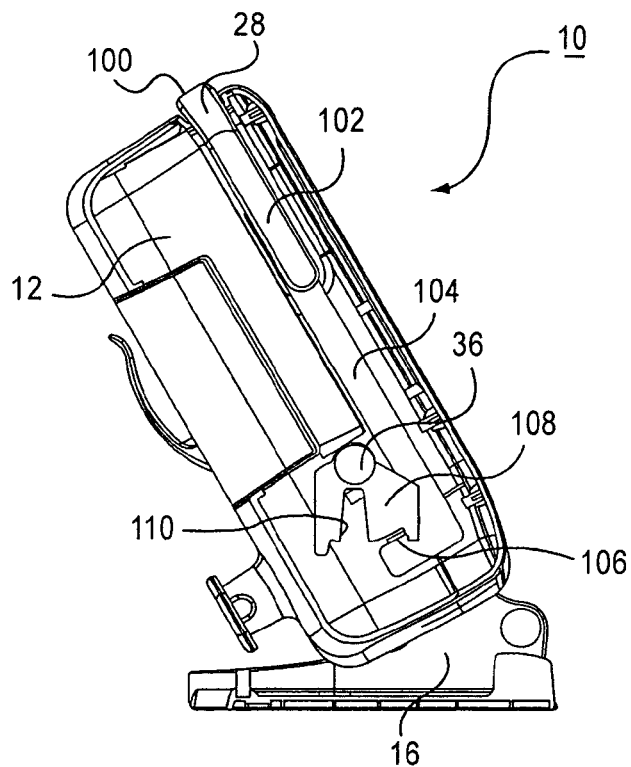
FIG. 12 is a see-through view showing an inside of the body.

FIG. 12 is a see-through view showing a part of an internal structure of the ultrasound diagnostic apparatus 10. Similar to FIG. 8, FIG. 10 shows a state in which the body is backwardly tilted to a maximum angle, and the operation panel 14 is not shown. The handle 28 is placed on the upper surface of the box shape of the body 12. The handle 28 comprises an upper surface portion 100 which extends along an entire width of the upper surface of the body and side surface portions 102 which extend downwardly from both ends of the upper surface portion along the side surface of the body, and has an approximate U shape as a whole. As the operation of the handle 28, only sliding along a direction of extension of the side surface portion 102 is allowed. On a portion immediately inside from the side surface of the body, a slide rod 104 which extends in a direction matching a longitudinal direction of the side surface portion 102 of the handle is placed. The slide rod 104 is slidable along its longitudinal direction. The slide rod 104 and the handle 28 are engaged to allow relative sliding in a predetermined range, and integrally slide beyond this range. The slide rod 104 is a plate-shaped member having an approximate L-shape, extending toward a lower portion of the body and bent at the lower portion toward the back surface side of the body. On the tip of the horizontal portion of the L shape, a follower projection 106 which projects toward the front side in a direction through the sheet of the drawing is provided.

Furthermore, on an internal portion of the side surface of the body, a guide plate 108 which is fixed on the connecting frame 16 is provided. As shown in FIG. 12, the guide plate 108 is positioned at a front side of the slide rod 104, and the guide plate 108 and the slide rod 104 are placed such that essentially these members do not interfere with each other. However, the follower projection 106 of the slide rod exists within a plane defined by the guide plate 108. With an engagement relationship between the follower projection 106 and the guide plate 108, the movement of the slide rod 104 is limited. A guide channel 110 which receives the follower projection 106 is provided on the guide plate 108.

Figure 13:
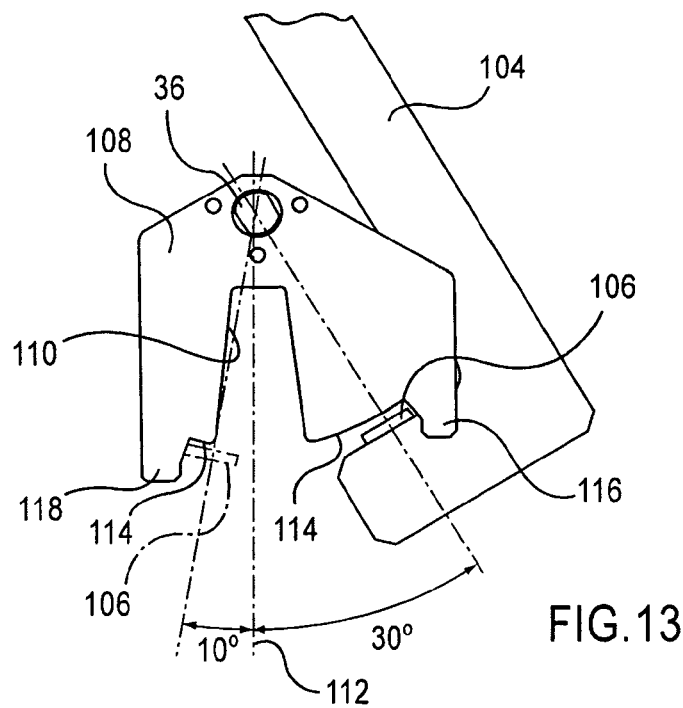
FIG. 13 is a diagram showing a relationship between a slide rod 104 and a guide plate 108, and particularly showing a state in which the body is backwardly tilted to a maximum angle.
Figure 14:
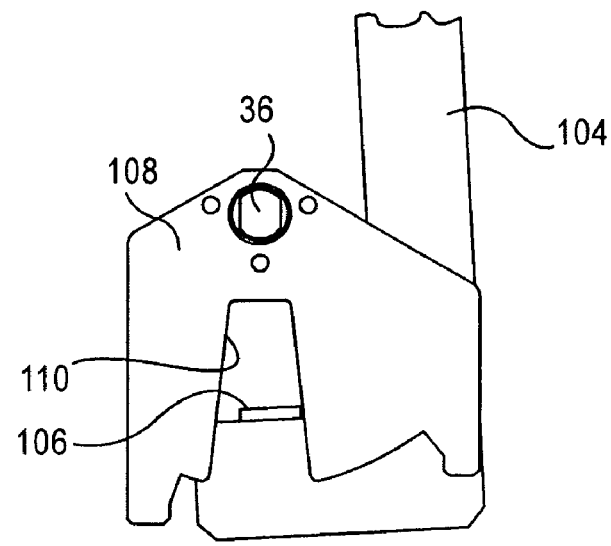
FIG. 14 is a diagram showing a relationship between a slide rod and a guide plate, and particularly showing a state of engagement of a follower projection 106 of the slide rod with a guide channel 110 of the guide plate.
Figure 15:
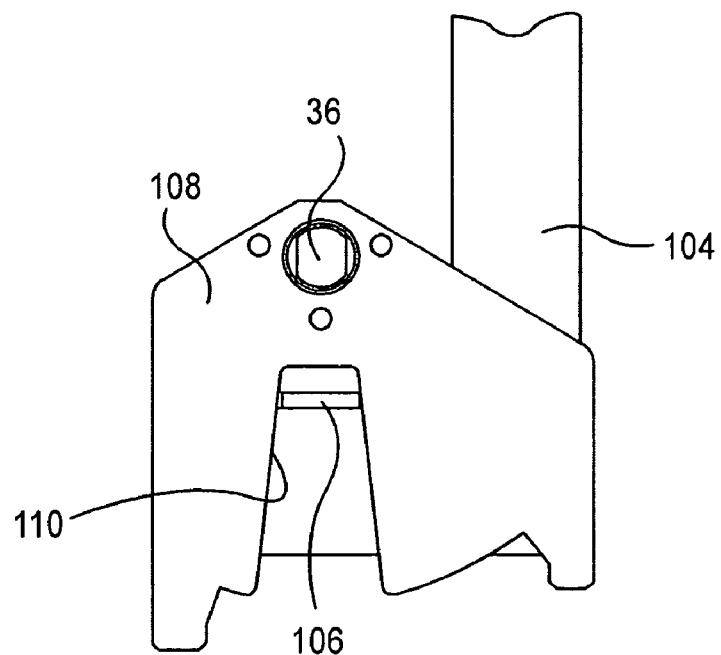
FIG. 15 is a diagram showing a relationship between a slide rod and a guide plate, and particularly showing a state in which the guide plate is raised to the maximum height.
Figure 16:
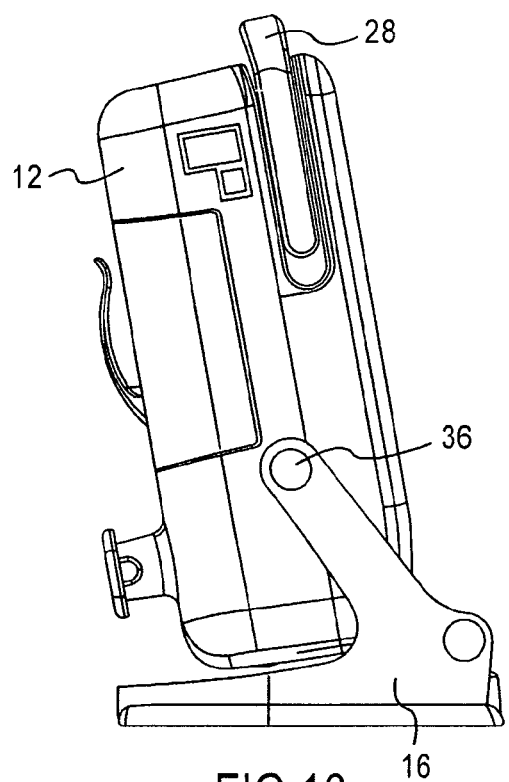
FIG. 16 is a side view of the apparatus corresponding to a state of FIG. 14.
Figure 17:
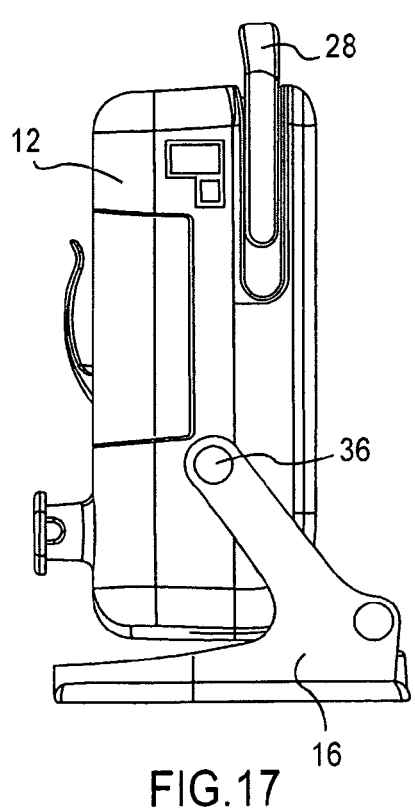
FIG. 17 is a side view of the apparatus corresponding to a state of FIG. 15.

FIGS. 13-15 are diagrams showing in detail the relationship between the guide plate 108 and the slide rod 104, in particular, between the guide plate 108 and the follower projection 106. FIG. 13 shows a state in which the body 12 is backwardly tilted to a maximum angle. FIG. 14 shows a state in which the body 12 is standing to approximate upright position, and shows a state in which the follower projection 106 is slightly inserted into the guide channel 110. A side view of the ultrasound diagnostic apparatus 10 in this state is shown in FIG. 16. FIG. 15 shows a state in which the body 12 is in the upright position and the handle 28 is raised to a maximum height. A side view of the ultrasound diagnostic apparatus 10 in this state is shown in FIG. 17.

The guide channel 110 of the guide plate 108 is opened in a downward direction in the figures, and, as will be described, receives the follower projection 106 in this opening. The guide channel 110 has a symmetrical shape with respect to a vertical line 112 through the axis of the body supporting stub 36 and is widened toward the opening. The angle of widening is, for example, 5° to the left and to the right. On both sides of the opening of the follower projection 106, edges 114 each having a shape of an arc of a circle centered at the axis of the body supporting stub 36 are provided, and stoppers 116 and 118 are provided on ends of the edge 114. The follower projection 106 is constrained by the edge 114 of the arc shape from moving in the upward direction beyond the edge 114. In addition, the follower projection 106 is also constrained by the stoppers 116 and 118 from moving in a direction along the edge 114. The movement of the pivoting direction is, for example, allowed up to 30° on the side of the stopper 116 and 10° on the side of the stopper 118. This range defines the pivoting range of the body 12, and corresponds to the backward tilt of 30° and the forward tilt of 10°.

If the body 12 is tilted when the ultrasound diagnostic apparatus 10 is to be carried, the body 12 is set to the upright state and the operation panel 14 is also set to the upright state. As described before, when the operation panel 14 is upright, the body 12 is also upright. However, it is possible for only the body to be upright. First, the handle 28 is raised from the backward tilt state of FIG. 12. In this process, because the follower projection 106 is constrained in its movement by the edge 114 of the guide plate 108, sliding of the slide rod 104 is blocked. Because of this, the handle 28 moves in the above-described range in which the relative movement with respect to the slide rod 104 is allowed, and the upper surface portion 100 of the handle 28 becomes slightly distanced from the body 12. If a finger is placed on the handle 28 and the handle 28 is further raised in the vertical direction, the body 12 stands, and the follower projection 106 moves to the position of the opening of the guide channel 110 along the edge 114. At this position, the follower projection 106 does not engage with the edge 114, and sliding of the slide rod 104 is permitted.

FIG. 14 shows a state in which the slide rod 104 is moved by a force to pull the handle 28 and the follower projection 106 is inserted into the guide channel 110. As the handle 28 is raised, the follower projection 106 is inserted deeper into the guide channel 110. The follower projection 106 is guided by the side surface of the guide channel, and a state is reached in which both side surfaces of the follower projection 106 contact both side surfaces of the guide channel 110. FIG. 15 shows this state. In this process, the body 12 is set in an upright state and in the position of the storage state. In addition, because the follower projection 106 is constrained by the guide channel 110, the pivoting action of the body 12 is locked. In other words, when the handle 28 is raised, the body 12 is set such that the body 12 cannot pivot. Therefore, during carriage in which the handle 28 is raised, the body 12 is locked to not pivot with respect to the connecting frame 16 and the operation panel 14.

An operation when the body 12 is raised from a backwardly tilted state has been described. An operation to raise the body from the forwardly tilted state is similar.

When the ultrasound diagnostic apparatus 10 is set to the storage state, the pivoting of the body 12 by the operation panel 14 and the raising of the handle 28 may be carried out together. In other words, in this configuration, with the operation to raise the operation panel 14, the body 12 rises to a state near the upright state, and with further raising of the handle 28, the body 12 is set to the upright state and locked in this state. It is desirable that, in the state in which the body 12 is raised up by the operation panel 14, the follower projection 106 is at the position opposing the opening of the guide channel 110. With this structure, when the handle 28 is raised, the follower projection 106 can immediately be inserted into the guide channel 110.

The operation panel 14 may pivot in a direction to open the operation panel 14 due to the weight of the operation panel 14 itself when the operation panel 14 is opened or closed, and it is desirable that the speed of the pivoting is not too large. However, if the pivoting by the weight is to be inhibited by friction, the force required for opening or closing the operation panel 14 may become large. In the ultrasound diagnostic apparatus 10 of the present embodiment, an inhibition by friction and inhibition by an elastic force are combined in order to inhibit pivoting of the operation panel 14 due to its weight.

Figure 18:
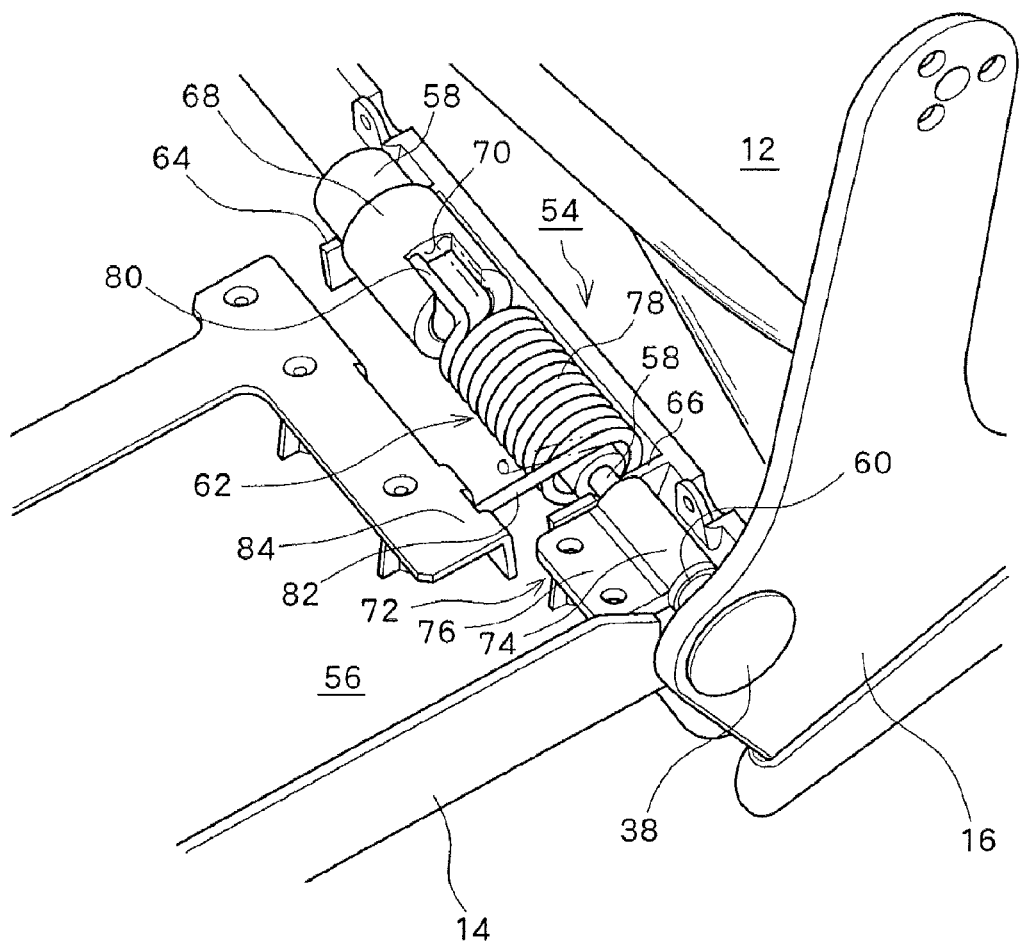
FIG. 18 is a perspective view of an inside of an operation panel showing a torque applying mechanism.

FIG. 18 is a diagram showing in detail a mechanism which applies a torque to the operation panel 14 (hereinafter referred to as a torque applying mechanism 54), incorporated in the operation panel supporting stub 38. FIG. 18 is a diagram in which the panel member on the front side is not shown and a panel member 56 on a back side (hereinafter referred to as a backside panel member 56) is shown, in order to show an internal structure of the operation panel 14.

The torque applying mechanism 54 comprises a hinge shaft 58 which is fixed on the connecting frame 16, a frictional bush 60 which applies a frictional torque to the hinge shaft 58, and a torsion spring 62 which is placed between the hinge shaft 58 and the operation panel 14. The hinge shaft 58 is rotatably held on holding ribs 64 and 66 provided on two locations on the operation panel 14. Although FIG. 18 only shows the portions of the holding ribs 64 and 66 which are provided on the backside panel member 56, ribs are also provided on the panel member on the front side to oppose the ribs shown in FIG. 18, and the hinge shaft 58 is held by pinching with the ribs. The hinge shaft 58 comprises portions through which the frictional bush 60 and the torsion spring 62 pass and a large-diameter portion 68 having a larger diameter than these portions. A recess 70 is formed on an outer peripheral surface of the large-diameter portion 68.

The frictional bush 60 is held in a bush holder 72 which is fixed to the backside panel member 56. The bush holder 72 comprises a holding tube 74 which stores the frictional bush 60 in the holding tube 74 and holds the frictional bush 60 and a fixture piece 76 which extends from the holding tube toward the outside in the radial direction. The fixture piece 76 is fixed to the backside panel member 56 by a screw or the like. When the backside panel member 56, that is, the operation panel 14, pivots, the bush holder 72 and the frictional bush 60 which are fixed to the backside panel member 56 also rotate. With this operation, a frictional torque is generated between the frictional bush 60 and the hinge shaft 58 passing through the frictional bush 60. In other words, the frictional bush 60 applies a torque to the operation panel such that the pivoting of the operation panel 14 is blocked or a resistance is provided against the pivoting.

The torsion spring 62 comprises a helical portion 78 which is placed coaxially with the hinge shaft 58, a first end 80 which extends from the helical portion in parallel to the hinge shaft 58, and a second end 82 which extends from the helical portion in a direction diverting from the hinge shaft. The first end 80 is positioned within the recess 70 provided on the large-diameter portion 68 of the hinge shaft 58. In the recess 70, a large distance is set between the end surfaces in the circumferential direction, to allow movement of the first end 80 in the circumferential direction. Therefore, the large-diameter portion 68 which is fixed on the connecting frame 16 engages the first end 80 of the torsion spring with play. The second end 82 of the torsion spring 62 engages an engagement plate 84 which is fixed on the rear side panel member 56.

Figure 19:
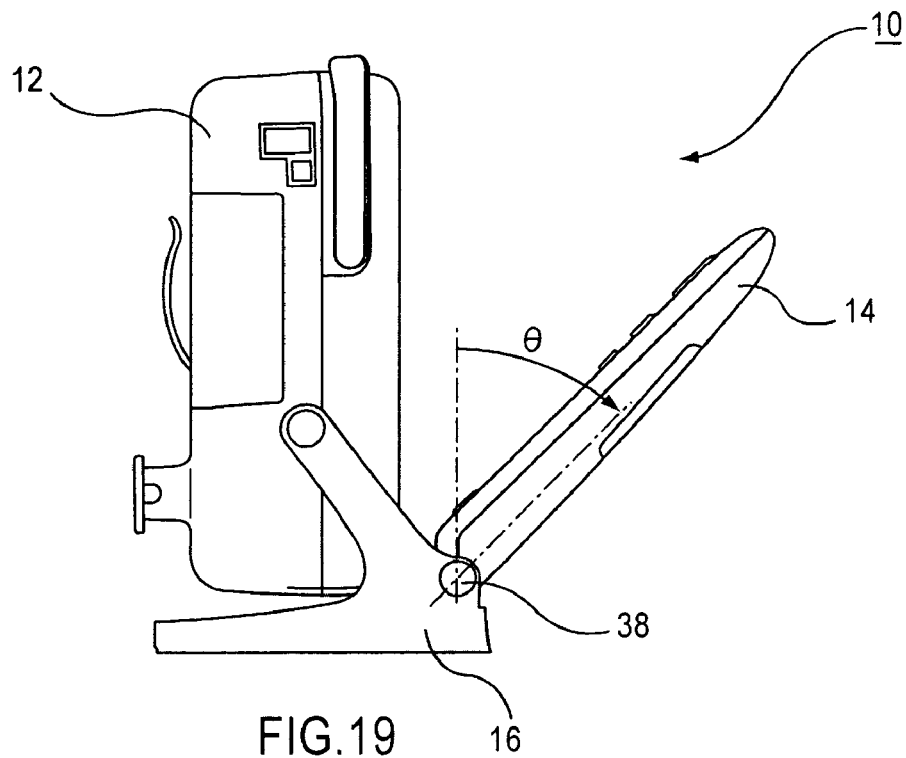
FIG. 19 is a side view showing a state during opening or closing of the operation panel.
Figure 20:
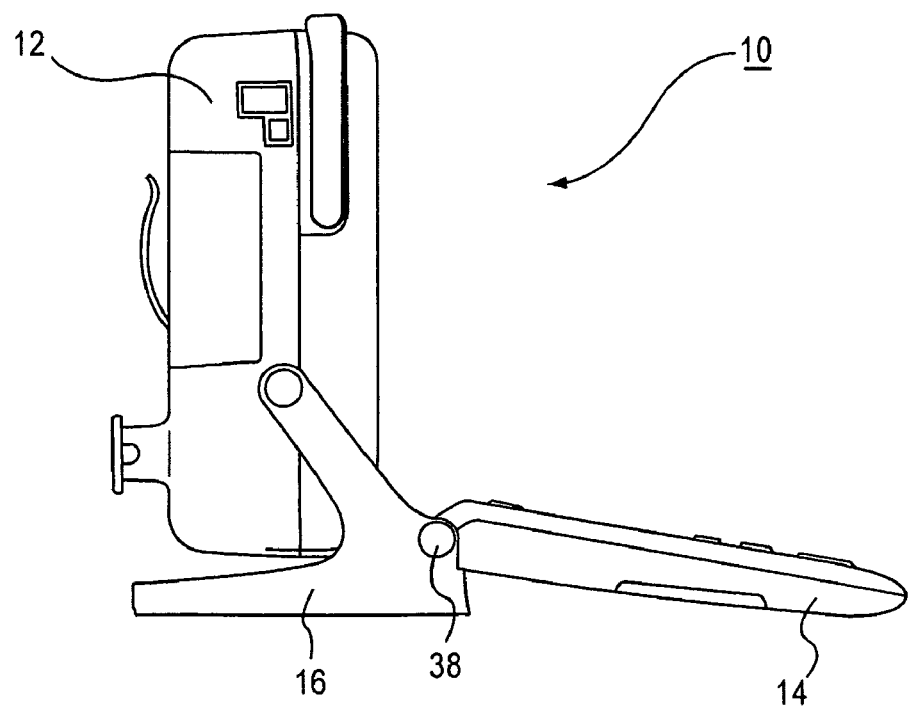
FIG. 20 is a side view showing a state in which the operation panel is opened.
Figure 21A:
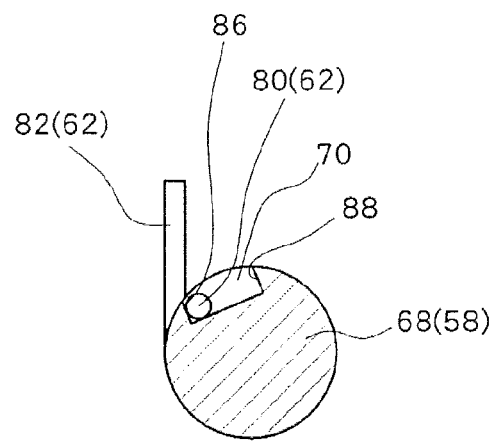
FIGS. 21A-21C are diagrams showing a relationship between a torsion spring and a large-diameter portion of a hinge shaft when the operation panel is opened or closed.
Figure 21B:
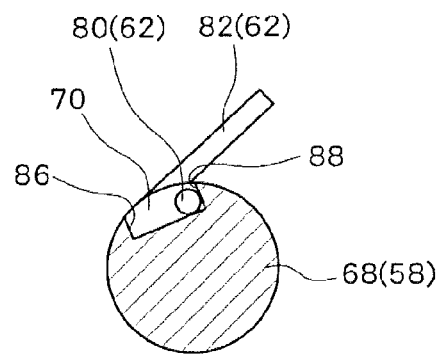
Figure 21C:
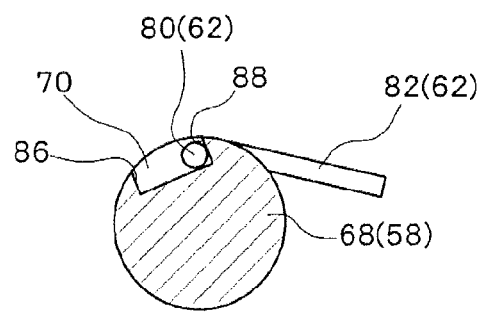
Figure 22:
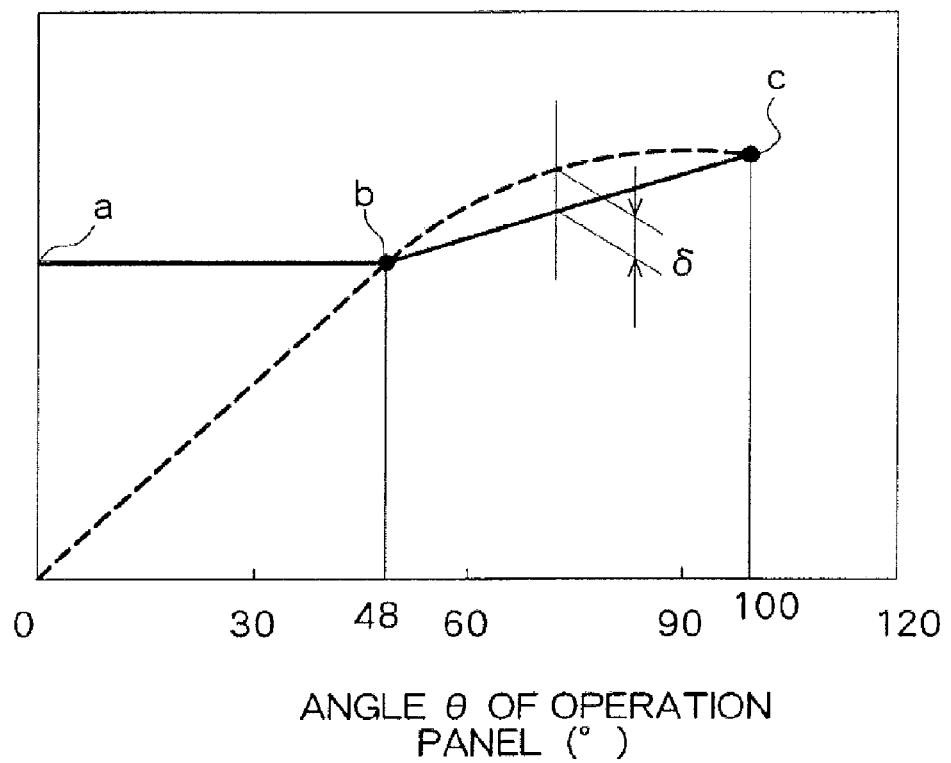
FIG. 22 is a diagram showing a torque acting on the operation panel 14.

FIGS. 10 and 19-22 are diagrams for explaining a torque acting on the operation panel 14 when the operation panel 14 is opened or closed. FIGS. 10, 19, and 20 are side views of the ultrasound diagnostic apparatus 10. FIG. 10 shows a storage state in which the operation panel 14 is upright and opposes the body 12. FIG. 19 is a diagram showing a state in which the operation panel 14 is pivoted from the storage state to an angle θ and FIG. 20 is a diagram showing a state of the operation panel 14 being pivoted and in the open state, which is a usage state. FIGS. 21A, 21B, and 21C are explanatory diagrams related to an action of the torsion spring 62 having the first end 80 and the second end 82. FIG. 22 is a diagram showing a torque which acts on the operation panel 14.

As shown in FIGS. 10, 19, and 20, the operation panel 14 can pivot between upright, a storage state (θ=0°) and an open state (θ=100°). In the ultrasound diagnostic apparatus 10, the transportability is improved by setting the operation panel 14 in the storage state and, during usage, on the other hand, the operation panel 14 is set to the open state. When the operation panel 14 is pivoted and opened, a torque in a direction to open the operation panel is generated around the operation panel supporting stub 38 due to the weight of the operation panel 14 itself. When the torque due to the weight is significant, the pivoting speed of the operation panel 14 becomes large, and there may be cases in which the impact when the operation panel contacts a surface on which the ultrasound diagnostic apparatus 10 is placed becomes large at the end of the opening process. The torque applying mechanism 54 of the ultrasound diagnostic apparatus 10 of the present embodiment generates a torque opposing the torque in the direction to open the operation panel due to the weight of the operation panel 14.

FIGS. 21A-21C show a relationship between the torsion spring 62 and the hinge shaft 58 when the operation panel is pivoted. FIG. 21A corresponds to the state of FIG. 10, FIG. 21B corresponds to FIG. 19, and FIG. 21C corresponds to FIG. 20. As described above, the first end 80 of the torsion spring is received in the recess 70 of the large-diameter potion. The recess 70 comprises a first end surface 86 and a second end surface 88 in the circumferential direction, and the first end 80 is allowed to move between the first and second end surfaces 86 and 88. In other words, the hinge shaft 58 and the torsion spring 62 engage each other with play corresponding to the allowed movement.

When the operation panel 14 is in the storage state, that is, in the state of FIG. 21A, the first end 80 is positioned on a side of the first end surface 86. Although FIG. 21A shows the first end 80 contacting the first end surface 86, the torsion spring 62 is in a free state, that is, in a state in which the twisting torque is not acting. Therefore, in the storage state, the first end 80 of the torsion spring does not need to be in contact with the first end surface 86 of the recess.

When the operation panel 14 is pivoted, the second end 82 of the torsion spring which is fixed by the engagement plate 84 on the operation panel is swiveled as shown in FIG. 21B. With this action, the entire torsion spring 62 is rotated, and the first end 80 moves to the other end surface 88 of the recess. After the play is taken up by this movement, the torsion spring 62 is twisted by the pivoting of the operation panel 14, and generates, as a reaction, a torque on the operation panel 14 in a direction to close the operation panel 14. In this manner, the second end surface 88 defines, by the first end 80 of the torsion spring being engaged and stopped, a boundary between a range of the play of the torsion spring 62 and a range in which an elastic force is to be acted.

In this manner, the torsion spring 62 does not generate a torque at an early stage of the pivoting during the opening operation of the operation panel 14 because of the play, and generates a torque in a direction to close the operation panel 14 corresponding to the pivot angle θ of the operation panel 14 between FIGS. 21B and 21C, after the play is taken up. In other words, after the play is taken up, the torsion spring 62 generates a torque which resists the torque due to the weight of the operation panel 14.

FIG. 22 is a diagram showing a torque acting on the operation panel 14. The torque by the weight of the operation panel 14 is shown with a dotted line, and the torque generated by the torque applying mechanism 54 or the like which resists the weight of the operation panel (hereinafter referred to as a resistive torque) is shown with a solid line. In FIG. 22, points a, b, and c correspond to FIGS. 21A, 21B, and 21C, respectively.

The resistive torque in an interval a-b is generated by a frictional torque by the frictional bush 60 and a frictional torque by other sliding members. The frictional torque is constant with respect to the pivot angle θ of the operation panel. When the pivot angle θ is increased, the frictional torque cannot sufficiently resist the torque by the weight of the operation panel. The torque by the torsion spring 62 acts in an interval b-c, and a torque in which the torque by the elastic force of the torsion spring 62 is added to the frictional torque described above acts as the resistive torque. The point b from which the resistive torque by the elastic force starts to act is set in the present embodiment to a point in which the resistive torque by friction matches the torque by the weight. In addition, a value of the resistive torque at the point where the operation panel 14 is completely opened (point c) is also set to match the torque due to the weight. This setting is realized by adjusting the position of the second end surface 88 of the recess of the large-diameter portion and the spring constant of the torsion spring.

The setting of the point where the resistive torque by the elastic force starts to act (point b) is determined such that the torque due to the friction does not become large in the interval a-b and that a difference between the torque due to the weight and the resistive torque does not become large in the interval b-c. If the friction torque is large in the interval a-b, a large force would be required for the operator to pivot the operation panel 14. In addition, if the difference between the torque due to the weight and the resistive torque is large in the interval b-c, the operation panel may pivot in the closing or opening direction without an operation by the operator. In general, it is desirable that the pivot angle θ of the operation panel be set in a range of 40° to 50°. In the present embodiment, θ is set to 48°.

The points b and c do not need to exist on a curve shown in FIG. 22 with a dotted line (torque due to the weight). If a maximum difference δ between a line segment b-c and the curve shown with the dotted line does not exceed the difference between a torque by a static friction and a torque by a kinetic friction in the interval b-c, the operation panel 14 can be maintained in the static state at any angle position in this interval. Therefore, the points b and c can be set to satisfy this condition.

As described, the ultrasound diagnostic apparatus 10 of the present embodiment is configured such that, when the operation panel 14 is opened, only the torque due to friction is acting in the early stage, and then the torque due to the elastic force is acting. With this configuration, it is possible to reduce the force required for the opening operation at the early stage of the opening operation, and at the same time, inhibit undesired movement of the panel by the torque due to the weight even when the torque due to the weight of the operation panel 14 becomes large.

The torque applying mechanism of the present embodiment can also be applied to an apparatus in which the body directly supports the operation panel.

Similar to a non-transportable ultrasound diagnostic apparatus, in a transportable ultrasound apparatus 10 also, an ultrasonic probe is connected to the body, for example, through a cable or the like. In the ultrasound diagnostic apparatus 10 of the present embodiment, a holder which stores the ultrasonic probe is provided.

FIG. 1 is again referred to. As described above, the holder 40 having the probe receptacle 42 and the jelly container receptacle 44 can be equipped on the arm portion 34 of the connecting frame 30. In addition, a neck portion 120 is formed between the probe receptacle 42 and the jelly container receptacle 44. FIG. 1 shows a state in which one ultrasonic probe is stored in the probe receptacle 42. An echo jelly container is stored in the jelly container receptacle 44. The jelly container receptacle 44 may be changed to a storage corresponding to the ultrasonic probe.

Figure 23:
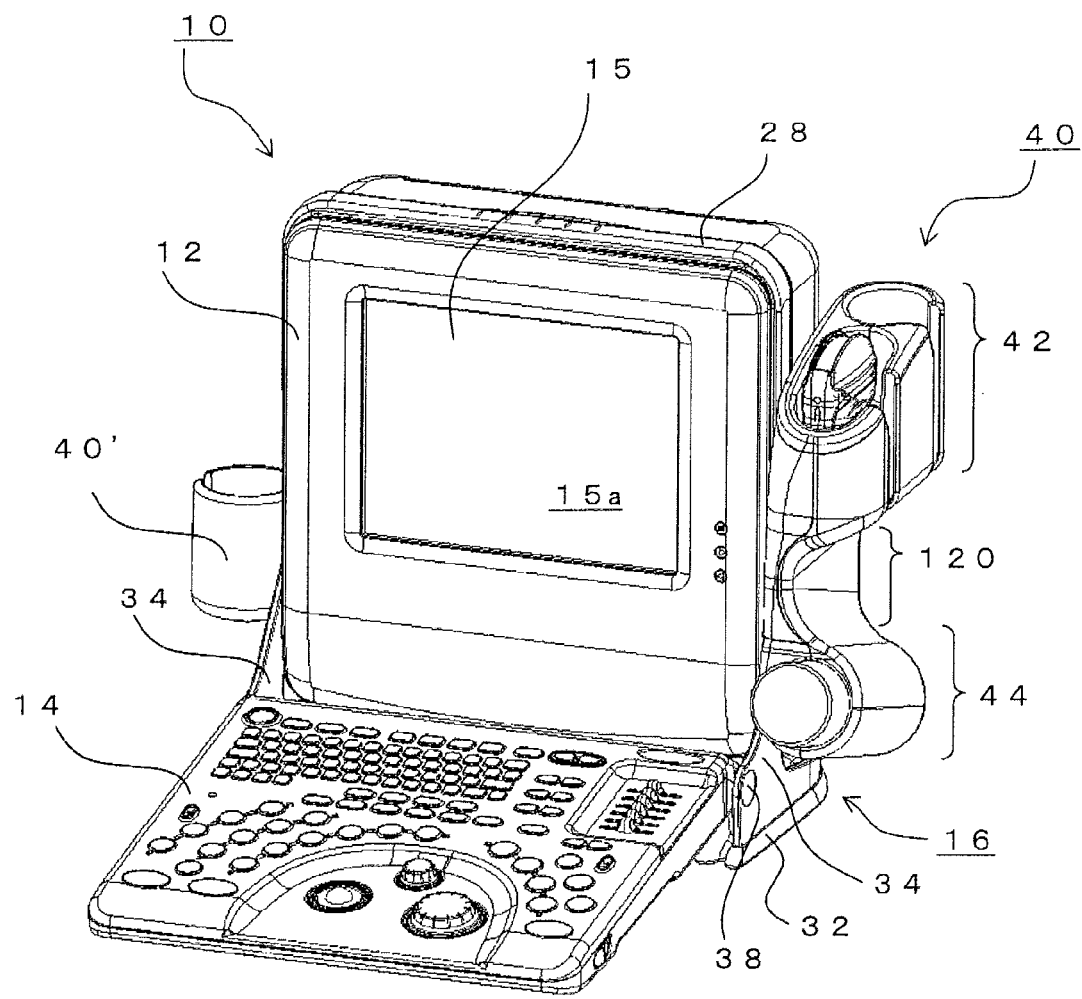
FIG. 23 is a perspective view showing a preferred embodiment of a holder of an ultrasound diagnostic apparatus.

As shown in FIG. 23, a holder 40' may be equipped on the arm portion 34 of the connecting frame 30 on the left side in the figure of the body 12. The holder 40' shown in FIG. 23 stores another ultrasonic probe. Alternatively, the holder 40 may be attached to the left side of the body 12. In this case, the shape or the like of the holder 40 is suitably changed to that corresponding to the left side. Similarly, the holder 40' may be attached on the right side of the body 12.

In the present embodiment, because the holders 40 and 40' are equipped on the connecting frame 30, the holders 40 and 40' do not move even when the body 12 and the operation panel 14 are pivoted, and can stably hold the ultrasonic probe and the echo jelly container. For example, even when the operation panel 14 is set to the upright position and to a closed position along the body 12 (storage state), the holders 40 and 40' do not move, and thus the ultrasonic probe and echo jelly container do not fall off from the holders 40 and 40'.

Similar to the non-transportable ultrasound diagnostic apparatus, in the transportable ultrasound diagnostic apparatus 10 of the present embodiment also, for example, an ultrasonic probe is connected to the body through a cable or the like. The probe cable of the stored ultrasonic probe may become an obstruction during carriage if the probe cable remains in a hung state from the probe holder.

As described above, the ultrasound diagnostic apparatus 10 may be set to the storage state by moving the operation panel 14 to an upright position and closing along the body 12. That is, the body 12 and the operation panel 14 can be closed with the display screen 15a of the display unit 15 of the body 12 and the operation surface of the operation panel 14 in the inside.

Figure 24:
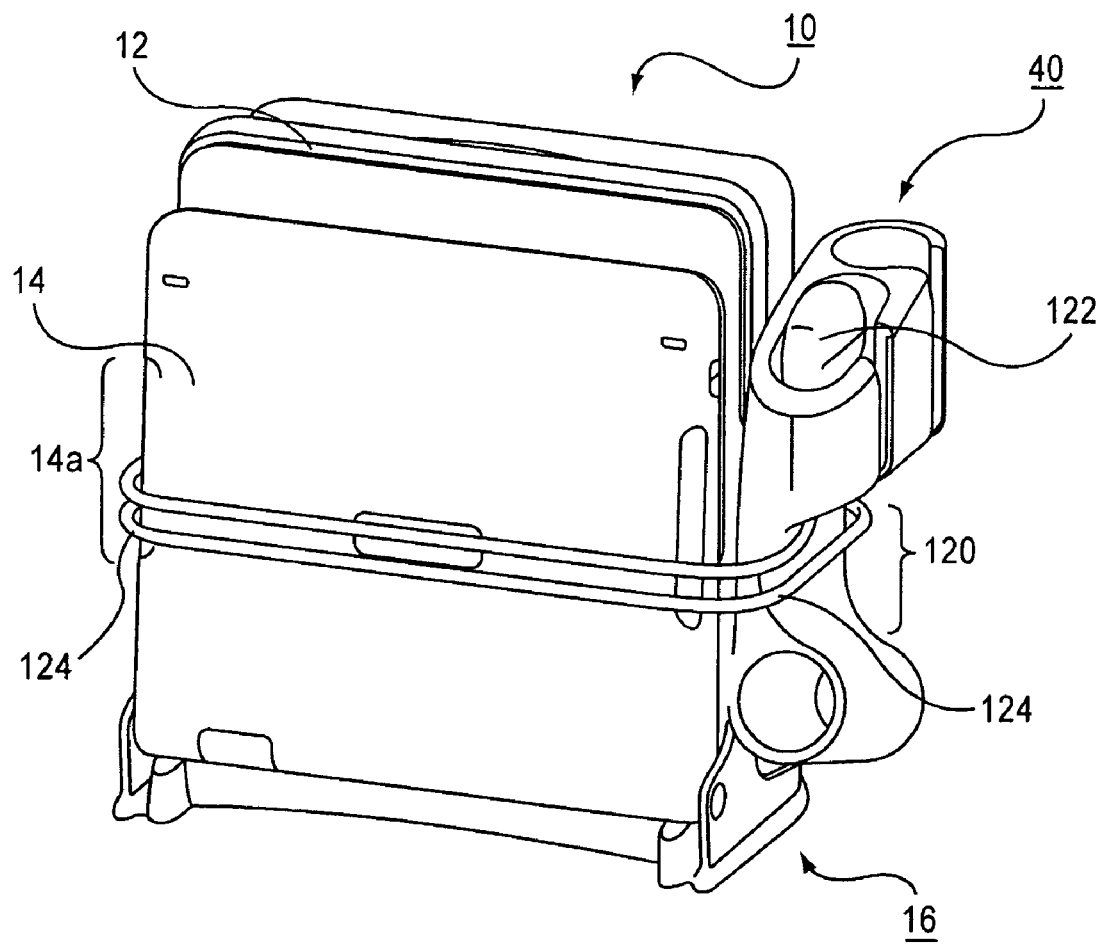
FIG. 24 is a front side perspective view of a state in which the operation panel is stored and a probe cable is wound.
Figure 25:
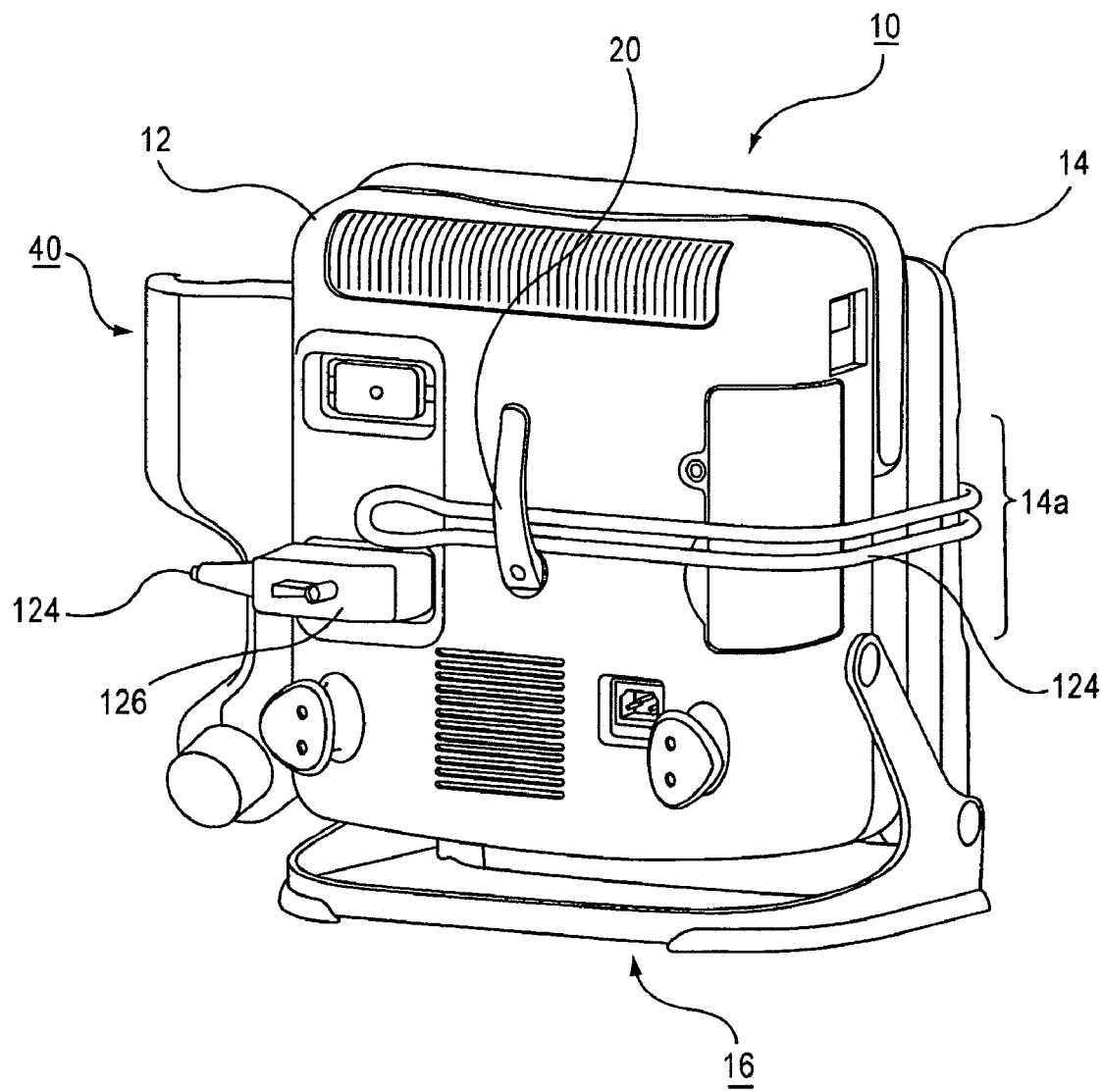
FIG. 25 is a back side perspective view of a state in which the operation panel is stored and a probe cable is wound.

FIGS. 24 and 25 are diagrams for explaining the storage state of the ultrasound diagnostic apparatus 10 of FIG. 1. FIG. 24 is a front side perspective view of the state in which the operation panel 14 is stored and FIG. 25 is a rear side perspective view of the state in which the operation panel 14 is stored.

As shown in FIGS. 24 and 25, in the present embodiment, the operation panel 14 can be pivoted to an approximate upright position, and a storage state can be achieved by moving the operation panel 14 to the upright position and closing along the body 12. In the storage state, a probe cable 124 of an ultrasonic probe 122 which is used in the ultrasound diagnostic apparatus 10 is stored while being wound around the body 12 and the operation panel 14, in a manner to bundle the closed body 12 and operation panel 14. The probe cable 124 is wound around the neck portion 120 of the holder 40.

As shown in FIG. 24, on the back surface of the operation panel 14, that is, on the surface which faces outside when the body 12 and the operation panel 14 are closed, a pit 14a corresponding to the probe cable 124 to be wound is provided. The pit 14a is provided on both right and left sides on the back surface of the operation panel 14.

As shown in FIG. 25, on the rear surface of the body 12, a hook 20 which hooks the wound probe cable 124 is provided. With the hook 20, the probe cable which is wound in a manner to bundle the body 12 and the operation panel 14 is fixed. One end of the probe cable 124 is connected to the ultrasonic probe 122 which is stored in the holder 40 and the other end of the probe cable 124 is connected to a probe connector 126 which is attached on the back surface of the body 12. The probe cable 124 is bent at an approximate center portion, and is fixed by the hook 20 near the bent portion.

In the present embodiment, because the probe cable 124 is stored while being wound around the body 12 and the operation panel 14 in a manner to bundle the closed body 12 and operation panel 14, the probe cable 124 can be cleanly stored and the ultrasound diagnostic apparatus 10 can be easily carried. In addition, even if a lock mechanism which closes the body 12 and the operation panel 14 is released accidentally, because the probe cable 124 is wound, it is possible to prevent the operation panel 14 from opening.

A preferred embodiment of the present invention has been described. The above-described embodiment, however, is merely exemplary in all aspects, and is not intended to limit the scope of the present invention. The present invention includes various modifications that fall within the scope and spirit of the present invention.

What is claimed is:

1. A transportable ultrasound diagnostic apparatus comprising:
    a body to which a display unit is integrated;
    an operation panel provided for an operation of the ultrasound diagnostic apparatus;
    a connecting member to which the body and the operation panel are pivotably linked around respective axes which differ from each other and which connects the body and the operation panel, the connecting member including a base portion that supports the body and the operation panel and an upwardly extending arm portion to which the body is pivotably connected so that the body can pivot around the axis;
    a guide plate attached to the connecting member, the guide plate including stopper projections; and
    a body projection that projects from the body and moves with the pivoting movement of the body,
    wherein the stopper projections constrain the movement of the body projection within a predetermined range thereby setting a range of pivoting movement of the body.

2. The transportable ultrasound diagnostic apparatus according to claim 1, wherein
    the connecting member can be placed on a flat surface and can support the body and the operation panel in a placed state.

3. The transportable ultrasound diagnostic apparatus according to claim 1, wherein
    the body and the operation panel can be set in a storage state in which the body and the operation panel are pivoted around the axes and are closed with a display screen of the display unit and an operation surface of the operation panel being inside, and an open state in which the body and the operation panel are opened so that the display screen faces a front side and the operation surface of the operation panel faces upward.

4. The transportable ultrasound diagnostic apparatus according to claim 3, wherein
    the body and the operation panel are in an upright state in the storage state.

5. The transportable ultrasound diagnostic apparatus according to claim 4, wherein
    a handle for carriage is provided on a surface of the body which becomes an upper section in the storage state.

6. The transportable ultrasound diagnostic apparatus according to claim 1, wherein
the axis around which the operation panel is pivoted extends horizontally; and
the transportable ultrasound diagnostic apparatus further comprises:
a frictional torque applying unit which applies a frictional torque which resists an opening operation of the operation panel and which blocks pivoting of the operation panel due to a weight of the operation panel until the operation panel is opened to a first angle; and
an elastic torque applying unit which applies a torque due to an elastic force in a closing direction of the operation panel when the operation panel is opened to an angle of greater than or equal to a second angle.

7. The transportable ultrasound diagnostic apparatus according to claim 6, wherein
the elastic torque applying unit comprises:
a spring member which generates an elastic force;
a connecting member side holder which engages one end of the spring member to the connecting member; and
an operation panel side holder which engages the other end of the spring member to the operation panel; and
play is provided in at least one of the connecting member side holder and the operation panel side holder between the holder and the end of the spring member, so that the elastic force does not act between the connecting member and the operation panel due to the play until the operation panel opens to the second angle and the play is taken up, and the elastic force acts when the operation panel opens to an angle greater than or equal to the second angle.

8. The ultrasound diagnostic apparatus according to claim 7, wherein
the frictional torque applying unit comprises:
a hinge shaft which is fixed on the connecting member and which is placed coaxially with the pivoting axis, and
a frictional bush which is fixed on the operation panel and through which a hinge shaft passes, and which generates a frictional torque with the hinge shaft;
the spring member of the elastic torque applying unit is a torsion spring having a helical portion placed coaxially with the pivoting axis; and
the connecting member side holder has a pair of engagement surfaces which is fixed on the hinge shaft, defines an angle range through which the one end of the torsion spring can move, and provides the play.

9. The transportable ultrasound diagnostic apparatus according to claim 6, wherein
when the operation panel opens to an angle of greater than or equal to the second angle, the pivoting position of the operation panel is maintained by the torque due to the frictional torque applying unit and by the torque due to the elastic torque applying unit.

10. The transportable ultrasound diagnostic apparatus according to claim 6, wherein
the first angle and the second angle are equal to each other.

11. The transportable ultrasound diagnostic apparatus according to claim 1, further comprising:
a hinge shaft which is placed on the axis around which the operation panel pivots;
a frictional bush which is fixed on the operation panel, through which the hinge shaft is inserted, and which generates a frictional torque through a relative rotation with the hinge shaft; and
a torsion spring which has a helical portion through which the hinge shaft passes, a first end which extends from the helical portion in parallel to the hinge shaft, and a second end which extends from the helical portion in a direction diverting from the hinge shaft, wherein
the hinge shaft has a large-diameter portion which is thicker than a portion through which the torsion spring passes and which has a recess which receives the first end of the torsion spring, and the first end can be moved in the recess in the circumferential direction within a range defined by two end surfaces of the recess in the circumferential direction;
the operation panel comprises an engagement plate which engages the second end of the torsion spring; and
the frictional torque generated by the frictional bush blocks pivoting of the operation panel due to a weight of the operation panel until the operation panel is opened to a predetermined angle, the first end of the torsion spring contacts one end surface of the recess receiving the first end when the operation panel is opened to the predetermined angle, and a torque is applied by the torsion spring in a direction to close the operation panel when the operation panel is opened to an angle of greater than or equal to the predetermined angle.

12. The transportable ultrasound diagnostic apparatus according to claim 1, wherein
the body and the operation panel can be pivoted to an upright state and can be closed, to result in a storage state, and
the operation panel pushes the body to pivot the body toward the upright state when the operation panel is closed.

13. The transportable ultrasound diagnostic apparatus according to claim 12, wherein
a panel front surface near a side on a rear side of the operation panel contacts a front surface of a housing of the body near a lower side and pivots the body.

14. The transportable ultrasound diagnostic apparatus according to claim 1, wherein
the body and the operation panel can be closed with a display screen of the display unit and an operation surface of the operation panel at the inside; and
a probe cable of an ultrasonic probe which is used in the transportable ultrasound diagnostic apparatus is wound around and fixed to the body and the operation panel in a manner to bundle the closed body and operation panel.

15. The transportable ultrasound diagnostic apparatus according to claim 14, wherein
the body has a hook which hooks the wound probe cable.

16. The transportable ultrasound diagnostic apparatus as recited in claim 1, wherein a height at which the body is supported is a height greater than or equal to ¼ of the height of the body and less than or equal to ½ of the height of the body.

17. A transportable ultrasound diagnostic apparatus comprising:
a body to which a display unit is integrated;
an operation panel provided for an operation of the ultrasound diagnostic apparatus; and
a connecting member to which the body and the operation panel are pivotably linked around axes which differ from each other and which connects the body and the operation panel,
wherein the body and the operation panel can be pivoted to an upright state and can be closed, to result in a storage state;
the transportable ultrasound diagnostic apparatus further comprises:

a handle which is placed on an upper portion of the body and which is raised and used during carriage;

a slide rod which engages the handle and slides along the body, and which has a follower; and a guide plate which is fixed to the connecting member and which has a guide channel which receives the follower; and when the follower is positioned within the guide channel, the follower moves in the guide channel with raising of the handle and is guided by the guide channel so that the body is pivoted to the upright state.

18. The transportable ultrasound diagnostic apparatus according to claim 17, wherein in a state in which the handle is raised, the follower is fixed and held in the guide channel and the body is fixed to the upright state.

19. The transportable ultrasound diagnostic apparatus according to claim 18, wherein during when the operation panel is closed, the operation panel pushes the body and pivots the body at least to a pivoting position in which the follower enters the guide channel.

20. A transportable ultrasound diagnostic apparatus, comprising:

a body to which a display unit is integrated;

an operation panel provided for an operation of the ultrasound diagnostic apparatus;

a connecting member to which the body and the operation panel are pivotably linked around axes which differ from each other and which connects the body and the operation panel;

a guide plate attached to the connecting member, the guide plate including stopper projections; and a body projection that projects from the body and moves with the pivoting movement of the body; and a holder attached to the transportable ultrasound diagnostic apparatus, wherein the stopper projections constrain the movement of the body projection within a predetermined range thereby setting a range of pivoting movement of the body, wherein the holder stores an ultrasonic probe of the ultrasound diagnostic apparatus, and wherein the holder is attached to the connecting member of the transportable ultrasound diagnostic apparatus.

21. The transportable ultrasound diagnostic apparatus according to claim 20, comprising:

a first storage unit which stores the ultrasonic probe;

a second storage unit which stores the ultrasonic probe or an echo jelly container; and a neck portion provided between the first storage unit and the second storage unit.

22. A transportable ultrasound diagnostic apparatus comprising:

a body to which a display unit is integrated;

an operation panel provided for an operation of the ultrasound diagnostic apparatus;

a connecting member to which the body and the operation panel are pivotably linked around axes which differ from each other and which connects the body and the operation panel;

a guide plate attached to the connecting member, the guide plate including stopper projections; and a body projection that projects from the body and moves with the pivoting movement of the body, wherein the stopper projections constrain the movement of the body projection within a predetermined range thereby setting a range of pivoting movement of the body, and wherein a holder which stores an ultrasonic probe can be attached to the connecting member.

23. A transportable ultrasound diagnostic apparatus, comprising:

a body to which a display unit is integrated;

an operation panel provided for an operation of the ultrasound diagnostic apparatus;

a connecting member to which the body and the operation panel are pivotably linked around axes which differ from each other and which connects the body and the operation panel;

a guide plate attached to the connecting member, the guide plate including stopper projections; and a body projection that projects from the body and moves with the pivoting movement of the body, wherein the stopper projections constrain the movement of the body projection within a predetermined range thereby setting a range of pivoting movement of the body, wherein the body and the operation panel can be closed with a display screen of the display unit and an operation surface of the operation panel at the inside; and a probe cable of an ultrasonic probe which is used in the transportable ultrasound diagnostic apparatus is wound around and fixed to the body and the operation panel in a manner to bundle the closed body and operation panel, and wherein the operation panel has a pit corresponding to the probe cable to be wound.

24. A transportable ultrasound diagnostic apparatus, comprising:

a body to which a display unit is integrated;

an operation panel provided for an operation of the ultrasound diagnostic apparatus;

a connecting member to which the body and the operation panel are pivotably linked around axes which differ from each other and which connects the body and the operation panel;

a guide plate attached to the connecting member, the guide plate including stopper projections; and a body projection that projects from the body and moves with the pivoting movement of the body, wherein the stopper projections constrain the movement of the body projection within a predetermined range thereby setting a range of pivoting movement of the body, wherein the body and the operation panel can be closed with a display screen of the display unit and an operation surface of the operation panel at the inside; and a probe cable of an ultrasonic probe which is used in the transportable ultrasound diagnostic apparatus is wound around and fixed to the body and the operation panel in a manner to bundle the closed body and operation panel, wherein a holder which stores the ultrasonic probe is attached to the connecting member, and a probe cable of the ultrasonic probe stored in the holder is wound in a manner to bundle the body, the operation panel, and the holder through a neck portion provided in the holder.

25. A transportable ultrasound diagnostic apparatus, comprising:
- a body to which a display unit is integrated;
- an operation panel provided for an operation of the ultrasound diagnostic apparatus; and
- a connecting member to which the body and the operation panel are pivotably linked around respective axes which differ from each other and which connects the body and the operation panel, the connecting member including a body supporting stub which pivotably supports the body,
- wherein the body and the operation panel can be set in a storage state in which the body and the operation panel are pivoted around the axes and are closed with a display screen of the display unit and an operation surface of the operation panel being inside, and an open state in which the body and the operation panel are opened so that the display screen faces a front side and the operation surface of the operation panel faces upward, and
- the operation panel and the body are adapted to apply a force on the body by the operation panel at a contact point where a moment is generated around a pivoting axis of the body supporting stub when the operation panel is closed.

* * * * *